US008759076B2

(12) United States Patent
Gulak et al.

(10) Patent No.: US 8,759,076 B2
(45) Date of Patent: Jun. 24, 2014

(54) METHOD AND APPARATUS FOR DETECTING AN ELECTRIC FIELD FLUCTUATION ASSOCIATED WITH THE PERMEABILIZATION OF A BACTERIAL CELL WALL

(76) Inventors: Patrick Glenn Gulak, Toronto (CA); Karen Lee Maxwell, Toronto (CA); Nasim Nikkhoo, Toronto (CA); Cintia Po Sze Man, Richmond (CA)

(*) Notice: Subject to any disclaimer, the term of this patent is extended or adjusted under 35 U.S.C. 154(b) by 1176 days.

(21) Appl. No.: 12/364,237

(22) Filed: Feb. 2, 2009

(65) Prior Publication Data

US 2009/0202985 A1 Aug. 13, 2009

Related U.S. Application Data

(60) Provisional application No. 61/025,522, filed on Feb. 1, 2008.

(51) Int. Cl.
C12M 1/34 (2006.01)
C12Q 1/18 (2006.01)

(52) U.S. Cl.
USPC .................... 435/287.1; 435/32; 435/288.3

(58) Field of Classification Search
USPC ...................... 435/287.1, 32, 288.3
See application file for complete search history.

(56) References Cited

U.S. PATENT DOCUMENTS 7,229,754 B2    6/2007  Kish et al.
7,740,805 B2 *  6/2010  Parris ........................... 422/527
2003/0155966 A1 *  8/2003  Harrison ........................... 330/9
2004/0014054 A1 *  1/2004  Frey et al. ........................... 435/6
2005/0165461 A1 *  7/2005  Takeda et al. ................... 607/61
2006/0172279 A1 *  8/2006  Smela et al. ....................... 435/4
2007/0109116 A1 *  5/2007  Burr .......................... 340/539.12

OTHER PUBLICATIONS

N. Nikkhoo, et al., "A 0.18um CMOS Integrated Sensor for the Rapid Identification of Bacteria", ISSCC Digest of Technical Papers, pp. 336-337, Feb. 2008.
N. Nikkhoo, et al., "A CMOS Integrated Bacterial Sensor for Rapid Detection of *Pseudomonas aeruginosa*", Biomedical Circuits and Systems Conference, 2008 BioCAS, pp. 213-216, Nov. 2008.
M. Dobozi-King, et al., "Rapid detection and identification of bacterial: Sensing of phase-triggered ion cascade (SEPTIC)", Biological Physics and Chemistry, Jan. 2005.
D. V. Lim, et al. "Current and Developing Technologies for Monitoring Agents of Bioterrorism and Biowarfare", Clinical Microbiology Review, 2005, pp. 583-607, Oct. 2005.

(Continued)

*Primary Examiner* — William H Beisner
(74) *Attorney, Agent, or Firm* — Bereskin & Parr LLP/S.E.N.C.R.K., s.r.l.; Stephen Beney

(57) ABSTRACT

A sensor for detecting an electric field fluctuation associated with the permeabilization of a bacterial cell wall comprises a substrate, at least two electrodes integrated on the substrate, an amplifier integrated on the substrate, and a processor electrically connected to the amplifier to analyze the amplified signal. The substrate and the at least two electrodes define a well between the at least two electrodes, and the at least two electrodes being configured to generate a signal in response to an electric field fluctuation in close proximity to the well or the electrodes triggered when at least one antibacterial agent associated with the well contacts a cognate target. The amplifier is configured to generate an amplified signal in response to the signal. In addition, the processor is electrically connected to the amplifier to analyze the amplified signal.

36 Claims, 19 Drawing Sheets

(56) References Cited

OTHER PUBLICATIONS

O. Lazcka, et al., "Pathogen detection: A perspective of traditional methods and biosensors", Biosensors and Bioelectronics, vol. 22, pp. 1205-1271, 2007.

N.K. Petty, et al., "Biotechnological exploitation of bacteriophage research", Trends in Biotechnology, vol. 25, No. 1, pp. 7-15, Jan. 2007.

P. Leonard, et al., "Advances in biosensors for detection of pathogens in food and water", Enzyme and Microbial Technology [Enzyme Microb. Technol], vol. 32, No. 1, pp. 3-13, Jan. 2003.

L. Goodridge, et al., "Reporter bacteriophage assays as a means to detect foodborne pathogenic bacteria", Food Research International, vol. 35, pp. 863-870, 2002.

V. Nanduri, et al., "Phage as a molecular recognition element in biosensors immobilized by physical adsorption", Biosensors & Bioelectronics, vol. 22, No. 6, pp. 986-992, Jan. 15, 2007.

D.E. Bradley, "Ultrastructure of Bacteriophages and Bacteriocins", Bacteriological Reviews, pp. 230-314, Dec. 1967.

M.J. Weiss, et al., "Reduction of Membrane Potential, an Immediate Effect of Colicin K", Proceedings of the National Academy of Sciences of the United States of America, vol. 75, No. 5, pp. 2483-2487, May 1978.

Y. Uratani, et al., "Pyocin R1 Inhibits Active Transport in *Pseudomonas aeruginosa* and Depolarizes Membrane Potential", J. of Bacteriology, vol. 157, No. 2, pp. 632-636, Feb. 1984.

J.M. Gould, et al., "Studies on the Depolarization of the *Escherichia coli* Cell Membrane by Colicin E1", J. of Biological Chemistry, 1977, vol. 252, No. 15, pp. 5491-5497, Aug. 1977.

P. Boulanger, et al., "Characterization of Ion Channels Involved in the Penetration of Phage T4 DNA into *Escherichia coli* Cells", J. of Biological Chemistry, 1988, vol. 263, No. 20, pp. 9767-9775, Jul. 1988.

L. Letellier, et al., "Involvement of ion channels in the transport of phage DNA through the cytoplasmic membrane of *E. coli*", Biochimie, vol. 71, No. 1, pp. 167-174, 1989.

T. Neufeld, et al., "Combined Phage Typing and Amperometric Detection of Released Enzymatic Activity for the Specific Identification and Quantification of Bacteria", Analytical Chemistry 2003, vol. 75, No. 3, pp. 580-585, Feb. 1, 2003.

J.M. Barrie, et al., "Spatiotemporal Analysis of Prepyriform, Visual, Auditory, and Somesthetic Surface EEGs in Trained Rabbits", J. of Neurophysiology, vol. 76, No. 1, pp. 520-539, Jul. 1996.

W.J. Freeman, et al., "Spatial spectra of scalp EEG and EMG from awake humans", Clinical Neurophysiology, pp. 1053-1068, Feb. 2003.

W.L.C. Rutten, "Selective Electrical Interfaces with the Nervous System", Annu. Rev. Biomed. Eng., vol. 4, pp. 407-452, Aug. 2002.

R.R. Harrison, et al., "A Low-Power Low-Noise CMOS Amplifier for Neural Recording Applications", IEEE Journal of Solid-State Circuits, vol. 38, No. 6, Jun. 2003.

A. Wang, et al., "A 180mV FFT Processor Using Subthreshold Circuit Techniques", ISSCC Digest of Technical Papers, 2004.

S.R. Williams, et al., "Retargeting R-Type Pyocins to Generate Novel Bactericidal Protein Complexes", Applied and Environmental Microbiology, Jun. 2008, pp. 3868-3876.

Central Dental Ltd., http//www.centraldentalltd.com, pp. 15-26.

* cited by examiner

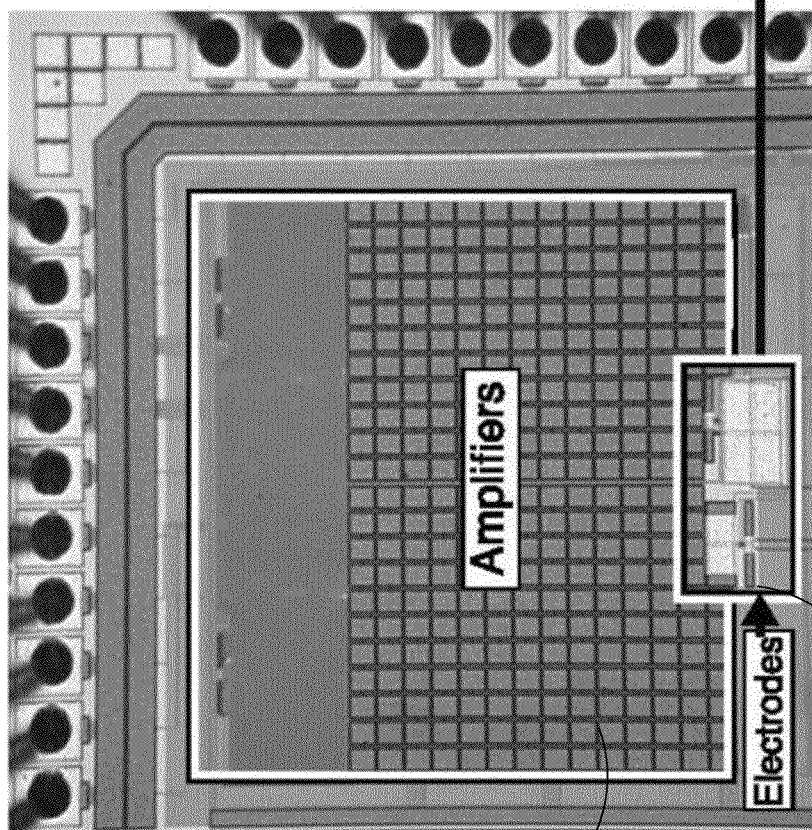
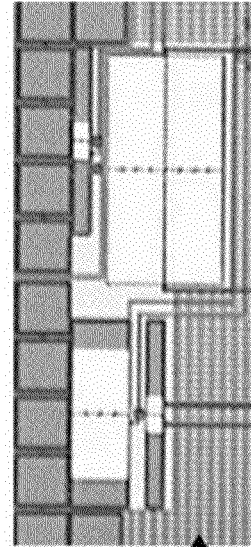
Figure 7A
Figure 7B
Figure 7C

METHOD AND APPARATUS FOR DETECTING AN ELECTRIC FIELD FLUCTUATION ASSOCIATED WITH THE PERMEABILIZATION OF A BACTERIAL CELL WALL

CROSS REFERENCES TO RELATED APPLICATIONS

This application claims priority from U.S. Provisional Application 61/025,522, filed on Feb. 1, 2008, which is incorporated herein by reference in its entirety.

The title and section headings used herein are for organizational purposes only and are not to be construed as limiting the subject matter described in any way.

FIELD

Applicants' teachings are related to a method and circuit for identifying bacteria and testing the effectiveness of antibacterial agents. More particularly, Applicants' teachings relate to a sensor for detecting an electric field fluctuation associated with the permeabilization of a bacterial cell wall.

SUMMARY

In various embodiments, applicants' teachings are related to a sensor for detecting an electric field fluctuation associated with the permeabilization of a bacterial cell wall. In some embodiments of applicants' teachings the sensor comprises a substrate, at least two electrodes integrated on the substrate, an amplifier integrated on the substrate, a processor electrically connected to the amplifier to analyze the amplified signal. The substrate and the at least two electrodes define a well between the at least two electrodes, and the at least two electrodes being configured to generate a signal in response to an electric field fluctuation in close proximity to the well or the electrodes triggered when at least one antibacterial agent associated with the well contacts a cognate target. The amplifier is configured to generate an amplified signal in response to the signal. In addition, the processor is electrically connected to the amplifier to analyze the amplified signal.

In some embodiments the permeabilization of the bacterial cell wall is permanent. In various other embodiments, the permeabilization of the bacterial cell wall is transient.

In various embodiments of applicants' teachings the antibacterial agent includes at least one bacteriophage. In other embodiments, the antibacterial agent includes at least one phage ghost. In some embodiments, the antibacterial agent includes at least one phage tail-like bacteriocin (PTLB). In various embodiments, the antibacterial agent includes at least one antimicrobial peptide. In some other embodiments of applicants' teachings, the antibacterial agent includes at least one bacteriophage lytic enzyme. In various other embodiments, the antibacterial agent includes at least one antibiotic. In some embodiments, the antibacterial agent includes at least one bacteriocidal antibiotic.

In various embodiments, the cognate target is selected from the group consisting of *Acinetobacter, Burkholderia, Legionella, Borrelia, Helicobacter, Parachlamydia, Bacteroides, Coxiella, Ehrlichia, Pasteurella, Porphyromonas,* and *Rickettsia*. In some other embodiments of applicants' teachings the cognate target comprises a bacteria, the bacteria being selected from the group consisting of *Enterobacter, Salmonella, Staphylococcus, Shigella, Listeria, Aerobacter, Klebsiella, Proteus, Pseudomonas, Streptococcus, Chlamydia, Mycoplasma, Pneumococcus, Neisseria, Clostridium, Bacillus, Corynebacterium, Mycobacterium, Campylobacter, Vibrio, Serratia, Providencia, Chromobacterium, Brucella, Yersinia, Haemophilus,* and *Bordetella*.

In some embodiments, the bacteriophage is selected from the group consisting of *S. mutans* phages, *Bacillus* phage .PHI.29, *Actinomyces* phages, bacteriophage M102, bacteriophage e10, bacteriophage f1, bacteriophage .lamda., bacteriophage PI, spherical phage PhiX174, spherical phage G4, spherical phage S13, bacteriophage T1, bacteriophage T2, bacteriophage T3, bacteriophage T4, bacteriophage T5, bacteriophage T6, bacteriophage T7, ssRNA bacteriophages MS2, ssRNA bacteriophages R17, ssRNA bacteriophages f2, and ssRNA bacteriophages Q beta.

In various embodiments of applicants' teachings, the processor is integrated on the substrate. In some embodiments, the processor performs an orthogonal transformation of the amplified signal. In various embodiments the orthogonal transformation may be one of: Wavelet Transform, Fourier, Walsh, Haar, Cosine, or Sine Transform as used in conventional DSP systems. In various embodiments, the orthogonal transformation is a Fast Fourier Transform (FFT). In some embodiments, the processor comprises at least one filter.

In some embodiments of the applicant's teachings, the processor performs various transformations of the amplified signal that includes FFT. In various embodiments, this transformation computes the power spectral density (PSD) of the amplified signal. In various embodiments, this transformation calculates the spectrogram of the amplified signal by computing PSD over a small time window of the amplified signal throughout the entire measurement interval. In various embodiments, the transformations are used to measure the concentration of the target.

In some embodiments of applicants' teachings, the processor comprises an energy measurement unit and at least one threshold detector. In some embodiments, the energy measurement unit is configured to measure the energy of the amplified signal. In various embodiments, the at least one threshold detector is configured to detect when the measured energy signal reaches a predetermined threshold.

In various embodiments, the processor comprises an energy measurement unit configured to measure the energy of the amplified signal and a classifier. In some embodiments, the processor further comprises analog components.

In some embodiments, the sensor comprises an analog to digital converter electrically connected to the amplifier, the analog to digital converter configured to digitize the amplified signal. In some embodiments, the analog to digital converter is integrated on the substrate.

In various embodiments, wherein the well is characterized by a distance between the at least two electrodes, the distance being between approximately 500 nanometers and approximately 50 micrometers. In some other embodiments, the well is characterized by a distance between the at least two electrodes, the distance being between approximately 20 nanometers and approximately 500 nanometers.

In various embodiments of applicants' teachings the substrate comprises a first substrate and a second substrate and the at least two electrodes are integrated on the first substrate and the amplifier is integrated on the second substrate. In some embodiments, the processor is integrated on the second substrate.

In some embodiments of applicants' teachings, the sensor comprises an analog to digital converter electrically connected to the amplifier and the processor, the analog to digital converter integrated on the second substrate and configured to digitize the amplified signal.

In various embodiments, the substrate is selected from the group consisting of silicon, single-crystal silicon, amorphous silicon, plastic, polymer, glass, sapphire, quartz, silica, silicon carbide, zinc oxide, magnesium oxide, manganese oxide, germanium, gallium nitride, gallium arsenide, gallium phosphide, indium phosphide, polysilicon, n-type diffusion semiconductor material, and p-type diffusion semiconductor material.

In some embodiments, the sensor further comprises a plurality of electrical connectors for electrically connecting the electrodes to the amplifier, each of the plurality of electrical connectors comprise at least one of a FET, JFET, MOSFET, OSFET, FinFET, bipolar transistor, amorphous silicon TFT, plastic transistor and organic transistor. As used herein, the term electrical connector may include, but is not limited to, contacts, vias, resistors, capacitors, and through-hole vias.

In various embodiments, the substrate, the at least two electrodes, the amplifier and the processor are co-integrated and fabricated in a CMOS process.

In some embodiments, the sensor further comprises: transistors integrated on and possibly in the substrate on top of which with various polysilicon and metal wiring layers separated by appropriate insulating layers fabricated above the substrate with appropriate vias and contacts and finally a top-layer passivation layer. In various embodiments, the passivation layer comprises a plurality of openings. In some embodiments, the electrodes are formed by strategic sized dimensions, placement and spacing of the metal layer and are exposed to the substrate through the plurality of openings that form the well between the at least two electrodes.

In some embodiments, the sensor comprises at least one noble metal which is applied to the at least two electrodes.

In various embodiments, the sensor comprises a plurality of electrical connectors for electrically connecting the at least two electrodes, the amplifier and the processor, where each of the plurality of electrical connectors are generated in accordance with CMOS circuit design techniques. As used herein, the term electrical connector may include, but is not limited to, contacts, vias, resistors, capacitors, and through-hole vias.

In various embodiments, the sensor comprises a power supply to power the sensor. In some embodiments, the power supply receives energy wirelessly from a remote location. In various embodiments, the sensor comprises at least one coupling capacitor configured to receive the energy through capacitive coupling. In some embodiments, the at least one coupling capacitor is integrated on the substrate. In various embodiments, the sensor further comprises a rectifier and a storage capacitor configured to rectify and store the received energy. In some embodiments, the storage capacitor is integrated on the substrate.

In various embodiments of applicants' teachings, the sensor further comprises at least one coupling inductor configured to receive the energy through inductive coupling. In some embodiments, the at least one coupling inductor is integrated on the substrate. In various embodiments, the sensor further comprises a rectifier and a storage capacitor configured to rectify and store the received energy. In some embodiments, the storage capacitor is integrated on the substrate.

In various embodiments, the sensor further comprising a wireless transmitter electrically connected to the processor, the wireless transmitter configured to transmit transmitting at least one of the amplified signal and the analyzed signal to a remote site.

In various embodiments, applicants' teachings are related to a kit for detecting an electric field fluctuation associated with the permeabilization of a bacterial cell wall. In some embodiments, the kit comprises a sensor and at least one bacteriophage. In some embodiments of applicants' teachings the sensor comprises a substrate, at least two electrodes integrated on the substrate, an amplifier integrated on the substrate, a processor electrically connected to the amplifier to analyze the amplified signal. The substrate and the at least two electrodes define a well between the at least two electrodes, and the at least two electrodes being configured to generate a signal in response to an electric field fluctuation in close proximity to the well or electrodes triggered when at least one antibacterial agent associated with the well contacts a cognate target. The amplifier is configured to generate an amplified signal in response to the signal. In addition, the processor is electrically connected to the amplifier to analyze the amplified signal. In various embodiments, the at least one bacteriophage is positionable in close proximity to the well or electrodes for triggering the electric field fluctuation when the at least one bacteriophage contacts a cognate target.

In various embodiments, the sensor further comprises an analog to digital converter electrically connected to the amplifier and the processor, the analog to digital converter configured to digitize the amplified signal.

In various embodiments, the cognate target is selected from the group consisting of *Acinetobacter, Burkholderia, Legionella, Borrelia, Helicobacter, Parachlamydia, Bacteroides, Coxiella, Ehrlichia, Pasteurella, Porphyromonas*, and *Rickettsia*. In some other embodiments of applicants' teachings the cognate target comprises a bacteria, the bacteria being selected from the group consisting of *Enterobacter, Salmonella, Staphylococcus, Shigella, Listeria, Aerobacter, Klebsiella, Proteus, Pseudomonas, Streptococcus, Chlamydia, Mycoplasma, Pneumococcus, Neisseria, Clostridium, Bacillus, Corynebacterium, Mycobacterium, Campylobacter, Vibrio, Serratia, Providencia, Chromobacterium, Brucella, Yersinia, Haemophilus*, and *Bordetella*.

In some embodiments, the bacteriophage is selected from the group consisting of *S. mutans* phages, *Bacillus* phage .PHI.29, *Actinomyces* phages, bacteriophage M102, bacteriophage e10, bacteriophage f1, bacteriophage .lamda., bacteriophage PI, spherical phage PhiX174, spherical phage G4, spherical phage S13, bacteriophage T1, bacteriophage T2, bacteriophage T3, bacteriophage T4, bacteriophage T5, bacteriophage T6, bacteriophage T7, ssRNA bacteriophages MS2, ssRNA bacteriophages R17, ssRNA bacteriophages f2, and ssRNA bacteriophages Q beta.

In various embodiments, applicants' teachings are related to a kit for detecting an electric field fluctuation associated with the permeabilization of a bacterial cell wall. In some embodiments, the kit comprises a sensor and at least one phage ghost. In some embodiments of applicants' teachings the sensor comprises a substrate, at least two electrodes integrated on the substrate, an amplifier integrated on the substrate, a processor electrically connected to the amplifier to analyze the amplified signal. The substrate and the at least two electrodes define a well between the at least two electrodes, and the at least two electrodes being configured to generate a signal in response to an electric field fluctuation in close proximity to the well or electrodes triggered when at least one antibacterial agent associated with the well contacts a cognate target. The amplifier is configured to generate an amplified signal in response to the signal. In addition, the processor is electrically connected to the amplifier to analyze the amplified signal. In various embodiments, the at least one phage ghost is positionable in close proximity to the well or electrodes for triggering the electric field fluctuation when the at least one phage ghost contacts a cognate target.

In various embodiments, applicants' teachings are related to a kit for detecting an electric field fluctuation associated with the permeabilization of a bacterial cell wall. In some embodiments, the kit comprises a sensor and at least one phage tail-like bacteriocin (PTLB). In some embodiments of applicants' teachings the sensor comprises a substrate, at least two electrodes integrated on the substrate, an amplifier integrated on the substrate, a processor electrically connected to the amplifier to analyze the amplified signal. The substrate and the at least two electrodes define a well between the at least two electrodes, and the at least two electrodes being configured to generate a signal in response to an electric field fluctuation in close proximity to the well or electrodes triggered when at least one antibacterial agent associated with the well contacts a cognate target. The amplifier is configured to generate an amplified signal in response to the signal. In addition, the processor is electrically connected to the amplifier to analyze the amplified signal. In various embodiments, the at least one phage tail-like bacteriocins (PTLB) is positionable in close proximity to the well or electrodes for triggering the electric field fluctuation when the at least one phage tail-like bacteriocin (PTLB) contacts a cognate target.

In various embodiments, applicants' teachings are related to a kit for detecting an electric field fluctuation associated with the permeabilization of a bacterial cell wall. In some embodiments, the kit comprises a sensor and at least one antimicrobial peptide. In some embodiments of applicants' teachings the sensor comprises a substrate, at least two electrodes integrated on the substrate, an amplifier integrated on the substrate, a processor electrically connected to the amplifier to analyze the amplified signal. The substrate and the at least two electrodes define a well between the at least two electrodes, and the at least two electrodes being configured to generate a signal in response to an electric field fluctuation in close proximity to the well or electrodes triggered when at least one antibacterial agent associated with the well contacts a cognate target. The amplifier is configured to generate an amplified signal in response to the signal. In addition, the processor is electrically connected to the amplifier to analyze the amplified signal. In various embodiments, the at least one antimicrobial peptide is positionable in close proximity to the well or electrodes for triggering the electric field fluctuation when the at least one antimicrobial peptide contacts a cognate target.

In various embodiments, applicants' teachings are related to a kit for detecting an electric field fluctuation associated with the permeabilization of a bacterial cell wall. In some embodiments, the kit comprises a sensor and at least one bacteriophage lytic enzyme. In some embodiments of applicants' teachings the sensor comprises a substrate, at least two electrodes integrated on the substrate, an amplifier integrated on the substrate, a processor electrically connected to the amplifier to analyze the amplified signal. The substrate and the at least two electrodes define a well between the at least two electrodes, and the at least two electrodes being configured to generate a signal in response to an electric field fluctuation in close proximity to the well or electrodes triggered when at least one antibacterial agent associated with the well contacts a cognate target. The amplifier is configured to generate an amplified signal in response to the signal. In addition, the processor is electrically connected to the amplifier to analyze the amplified signal. In various embodiments, the at least one bacteriophage lytic enzyme is positionable in close proximity to the well or electrodes for triggering the electric field fluctuation when the at least one bacteriophage lytic enzyme contacts a cognate target.

In various embodiments, applicants' teachings are related to a kit for detecting an electric field fluctuation associated with the permeabilization of a bacterial cell wall. In some embodiments, the kit comprises a sensor and at least one antibiotic. In some embodiments of applicants' teachings the sensor comprises a substrate, at least two electrodes integrated on the substrate, an amplifier integrated on the substrate, a processor electrically connected to the amplifier to analyze the amplified signal. The substrate and the at least two electrodes define a well between the at least two electrodes, and the at least two electrodes being configured to generate a signal in response to an electric field fluctuation in close proximity to the well or electrodes triggered when at least one antibacterial agent associated with the well contacts a cognate target. The amplifier is configured to generate an amplified signal in response to the signal. In addition, the processor is electrically connected to the amplifier to analyze the amplified signal. In various embodiments, the at least one antibiotic is positionable in close proximity to the well or electrodes for triggering the electric field fluctuation when the at least one antibiotic contacts a cognate target. In some embodiments, the at least one antibiotic is a bacteriocidal antibiotic.

In various embodiments, applicants' teachings are related to a method of utilizing the sensor according to applicants' teachings to characterize a hypothesized antibacterial agent. In some embodiments, the method comprise, positioning at least one known bacteria in close proximity to the well or electrodes, positioning the at least one hypothesized antibacterial agent in close proximity to the well or electrodes, monitoring electric field fluctuations in close proximity to the well, and characterizing the antibacterial agent based on the electric field fluctuations. In various embodiments, the antibacterial agent is selected from the group consisting of: bacteriophages, phage ghosts, antimicrobial peptides, bacteriophage lytic enzymes, phage tail-like bacteriocins, and antibiotics.

In various embodiments, applicants' teachings are related to a method of utilizing the sensor according to applicants' teachings to identify bacteria, the method comprising: positioning at least one known antibacterial agent in close proximity to the well or electrodes, positioning the at least one bacterium in close proximity to the well or electrodes, monitoring electric field fluctuations in close proximity to the well or electrodes, and identifying the at least one bacterium based on the electric field fluctuations. In various embodiments, the antibacterial agent is selected from the group consisting of: bacteriophages, phage ghosts, antimicrobial peptides, bacteriophage lytic enzymes, phage tail-like bacteriocins, and antibiotics.

In various embodiments, applicants' teachings are related to a method of utilizing the sensor according to applicants' teachings to determine the efficacy of an antibacterial agent. In some embodiments, the method comprises, positioning at least one known bacteria in close proximity to the well or electrodes, positioning the at least one hypothesized antibacterial agent in close proximity to the well or electrodes, monitoring electric field fluctuations in close proximity to the well, and determining the efficacy of the antibacterial agent based on the electric field fluctuations. In various embodiments, the antibacterial agent is selected from the group consisting of: bacteriophages, phage ghosts, antimicrobial peptides, bacteriophage lytic enzymes and antibiotics.

As used herein, the phrase "in close proximity to the well" includes positions within the well, as well as positions outside of the well and adjacent the well.

BRIEF DESCRIPTION OF THE DRAWINGS

The skilled person in the art will understand that the drawings, described below, are for illustration purposes only. The drawings are not intended to limit the scope of the applicants' teachings in any way.

FIG. 3a is a perspective view of a cross-section of a nanowell according to various embodiments of applicants' teachings;

FIG. 3b is a schematic view of the electrodes of FIG. 3a;

FIG. 4a is a schematic diagram of an amplifier of the sensor system of FIG. 2;

FIG. 4b is a detailed schematic diagram of an OTA of the amplifier of FIG. 4a;

FIG. 7a is a micrograph of the chip incorporating the electrodes and amplifier of FIG. 2;

FIG. 7b is an enlarged view of a portion of FIG. 7 showing the electrodes in greater detail;

FIG. 7c is a graph that lists specifications of the chip of FIG. 7a;

FIG. 10a is a perspective view of a cross-section of nanowell in accordance with Example 1 described hereinbelow;

FIG. 10b is a schematic view of the electrodes of the nanowell of FIG. 10a;

DETAILED DESCRIPTION

Various embodiments described herein relate to an integrated sensor for identifying bacteria that addresses drawbacks of traditional detection techniques by combining the specificity of phages with the sensitivity of integrated electronic circuits, using the principle reported in [1]. Various embodiments described herein also relate to an integrated sensor for identifying bacteria by combining the specificity of either phage ghosts or antimicrobial peptides, or bacteriophage lytic enzymes or antibiotics with the sensitivity of integrated electronic circuits. The embodiment described herein also relate to an integrated sensor for testing the effectiveness of antibacterial agents that attack bacterial cell walls. The embodiment described herein also relate to the isolation and characterization of bacteriophages, phage ghosts, antimicrobial peptides, bacteriophage lytic enzymes, or antibiotics.

Figures 1A, 1B, 1C:
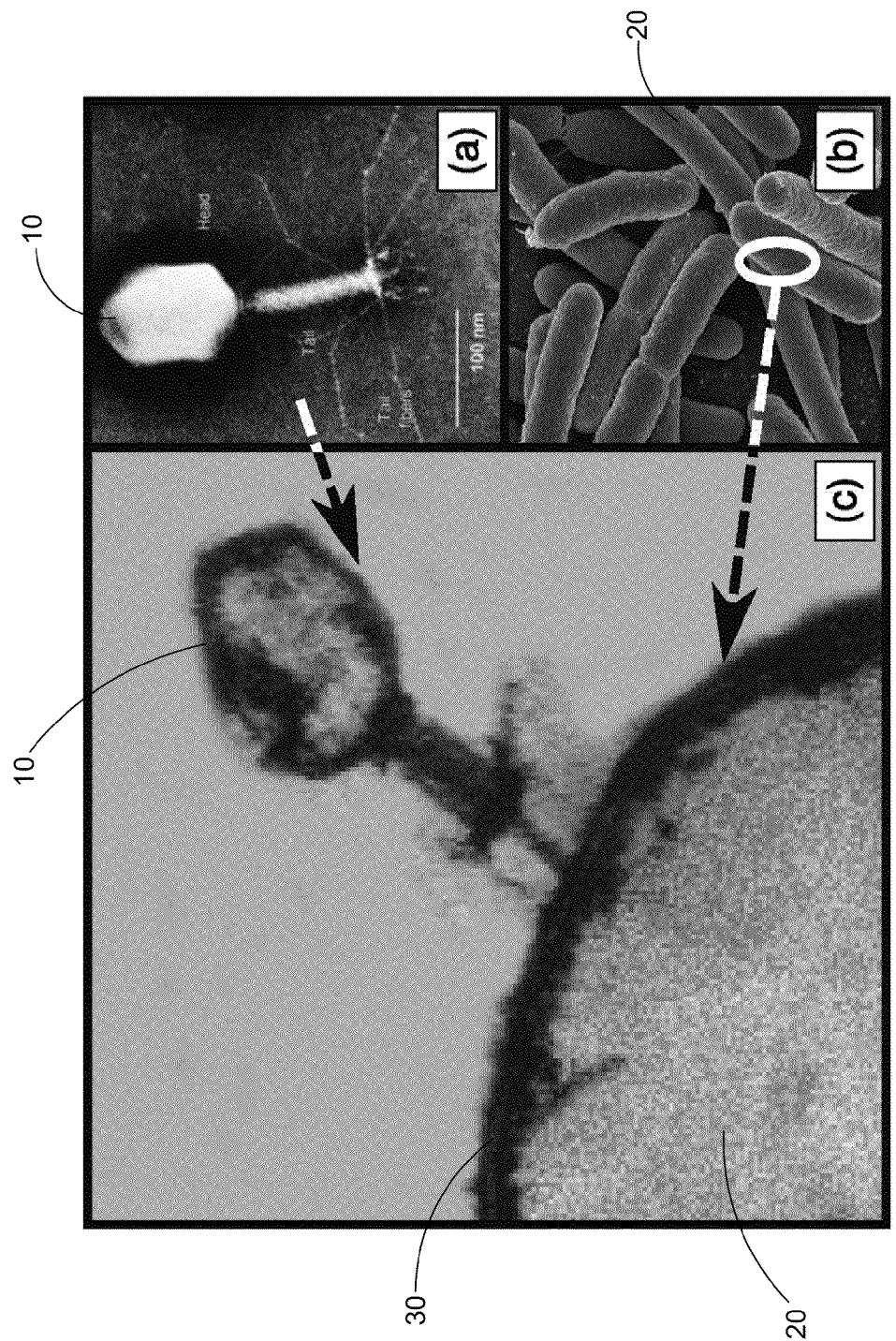
FIG. 1a is an electron micrograph of a T4 phage.
FIG. 1b is an electron micrograph of E. coli bacteria.
FIG. 1c is an electron micrograph showing T4 phage attachment to the E. coli cell wall.

There is widespread demand for a low-cost, rapid, selective and sensitive method for detecting bacteria in medical diagnosis, and food-safety inspection. Traditional methods, such as polymerase chain reaction and cell culture techniques take several hours to days to give accurate results, and require bulky, expensive equipment. Recently, a technology called "sensing of phage-triggered ion cascade" has been introduced [1], that uses bacteriophages (phages) as biological detecting elements, along with electrical-noise analysis to identify bacteria in less than 10 minutes. A phage is a type of virus that infects bacteria. They are ubiquitous in nature, easily produced, and do not require special storage or handling conditions. Phage libraries with specificities for a wide variety of bacteria of medical interest are commercially available. FIG. 1a shows an electron micrograph of a T4 phage 10 [4,5]. FIG. 1b illustrates an electron micrograph of *E. coli* bacteria 20. FIG. 1c illustrates an electron micrograph of a T4 phage 10 attached to the *E. coli* cell wall 30. When a phage attacks its specific bacterial host the tail interacts with the bacterial cell wall and its DNA is injected into the cell. During this infection process, there is a transitory efflux of ions from the cell, which creates strong electric-field fluctuations in the sample for several minutes. The fluctuations occur primarily in the frequency range of 1 to 10 Hz.

Figure 2:
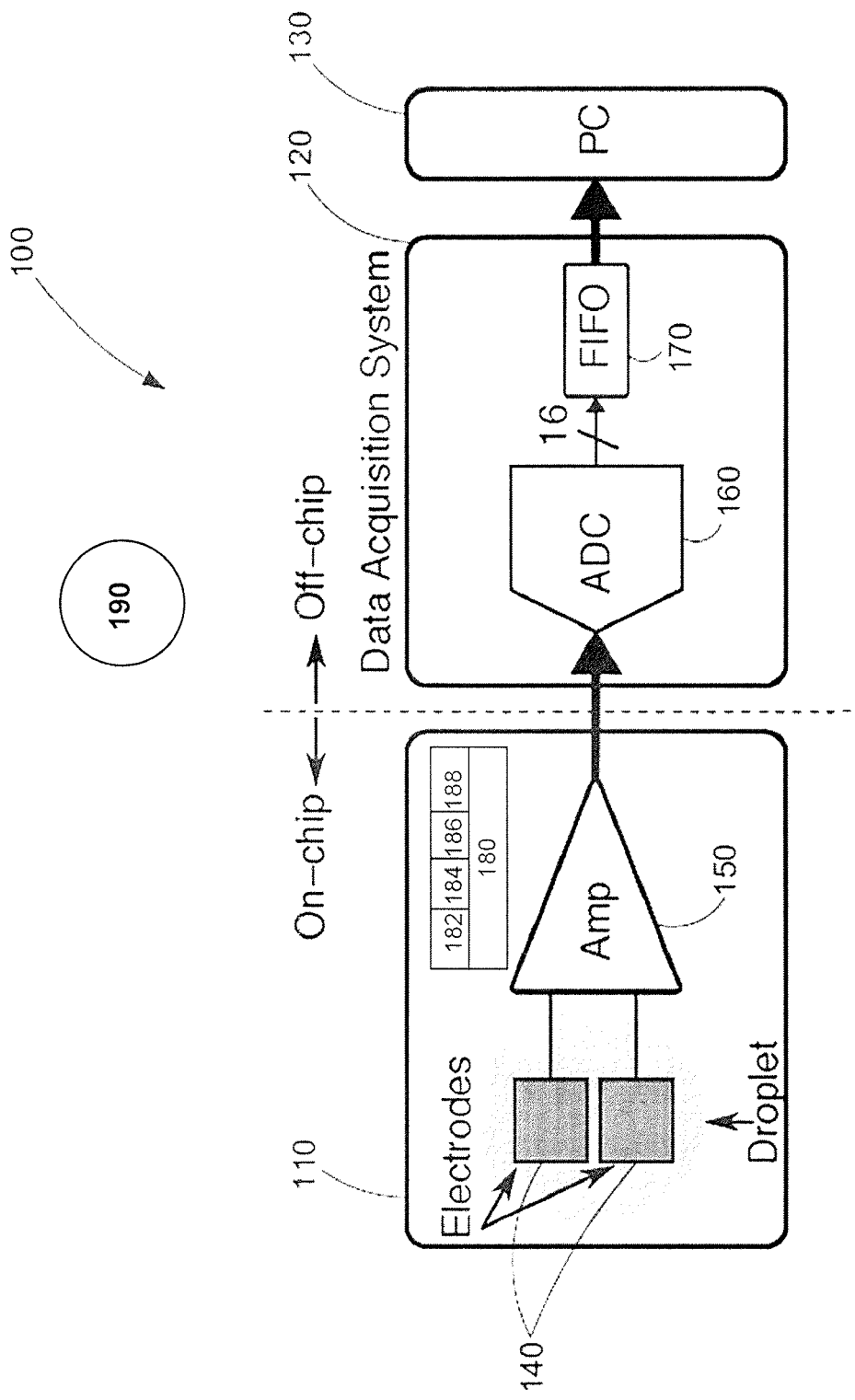
FIG. 2 is a block diagram of overall sensor system according to various embodiments of applicants' teachings.

FIG. 2 illustrates the overall block diagram of the sensor system 100. Sensor system 100 comprises an integrated sensor 110 a data acquisition system 120 and a computing device 130, which may for example be a personal computer. Integrated sensor 110 comprises at least two electrodes 140 and at least one integrated amplifier 150. The outputs of the integrated amplifiers 150 are connected to the off-chip data acquisition system 120 that digitizes the amplified signal and transfers the results to computing device 130 for analysis. Data acquisition device comprises and an analog to digital converter 160 and a buffer 170.

In various embodiments, integrated sensor 110 may be fabricated using a silicon-based implementation. In addition, in some embodiments, standard CMOS technology may be used. Furthermore, various embodiments of the integrated sensor 110 do not require noble-metal electrodes. Moreover, integrated sensor 110 co-integrates active circuitry on the same substrate as the measurement site containing the bacteria to reduce the noise and enhance the system sensitivity. In various embodiments, the sensor comprises a power supply (180) to power the sensor. Optionally, in some embodiments, power supply (180) receives energy wirelessly from a remote location (190). In various embodiments, the sensor optionally comprises at least one coupling capacitor (182) configured to receive the energy through capacitive coupling. In some embodiments, the at least one coupling capacitor (182) is integrated on the substrate. In various embodiments, the sensor further comprises a rectifier (184) and a storage capacitor (186) configured to rectify and store the received energy. In some embodiments, the storage capacitor is integrated on the substrate. In various embodiments the sensor further comprises at least one coupling inductor (188) configured to receive the energy through inductive coupling. In some embodiments, the at least one coupling inductor (188) is integrated on the substrate. In various embodiments, the sensor further comprises a rectifier (184) and a storage capacitor (186) configured to rectify and store the received energy. In some embodiments, the storage capacitor (186) is integrated on the substrate.

Figures 3A, 3B:
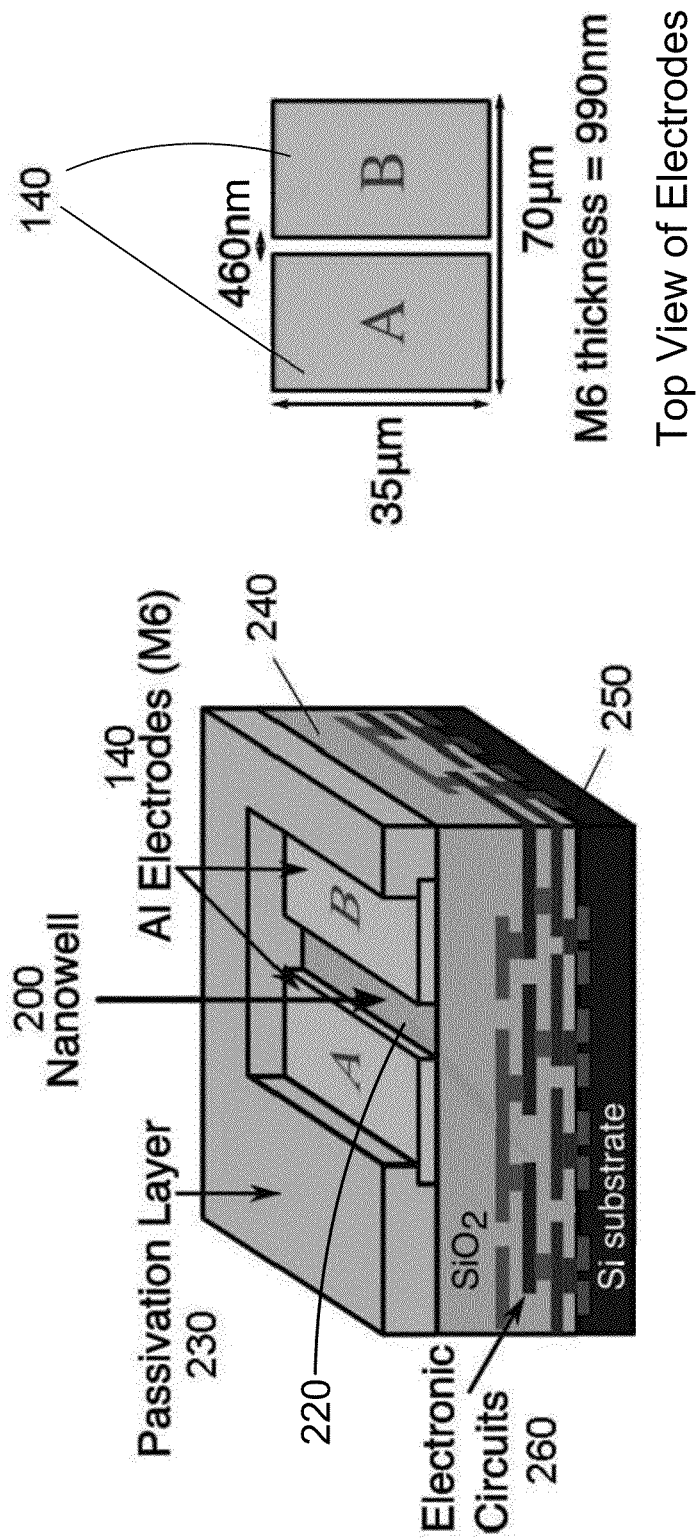

FIG. 3a shows the cross-section of the nanowell 200 used to sense the aforementioned voltage fluctuations. Nanowell 200 comprises two electrodes 140 and a trench 220. In some embodiments, which utilize the CMOS process electrodes 140 can be made from the top-layer metal. The top-layer material may be but is not limited to Aluminum, Copper, alloys of Aluminum, and alloys of Copper. The particular metal that is utilized in an embodiment may depend on such factors as whether the embodiment is intended to be a single-use or disposable device. For example, certain metals may not be suitable for more than a single use but can be adequate for a single use.

In addition, in embodiments that utilize the CMOS process, trench 220 can be made by removing the top passivation layer 230 using a passivation mask (not illustrated). In some embodiments, Nanowell 200 is co-integrated with a layer of silicon dioxide 240, a layer of silicon substrate 250, and electronic circuits 260 integrated within the silicon dioxide 240 and silicon substrate 250. FIG. 3b defines exemplary dimensions and separation of the electrodes for various example embodiments. These dimensions were used in measurements that will be described below.

Figures 4A, 4B:
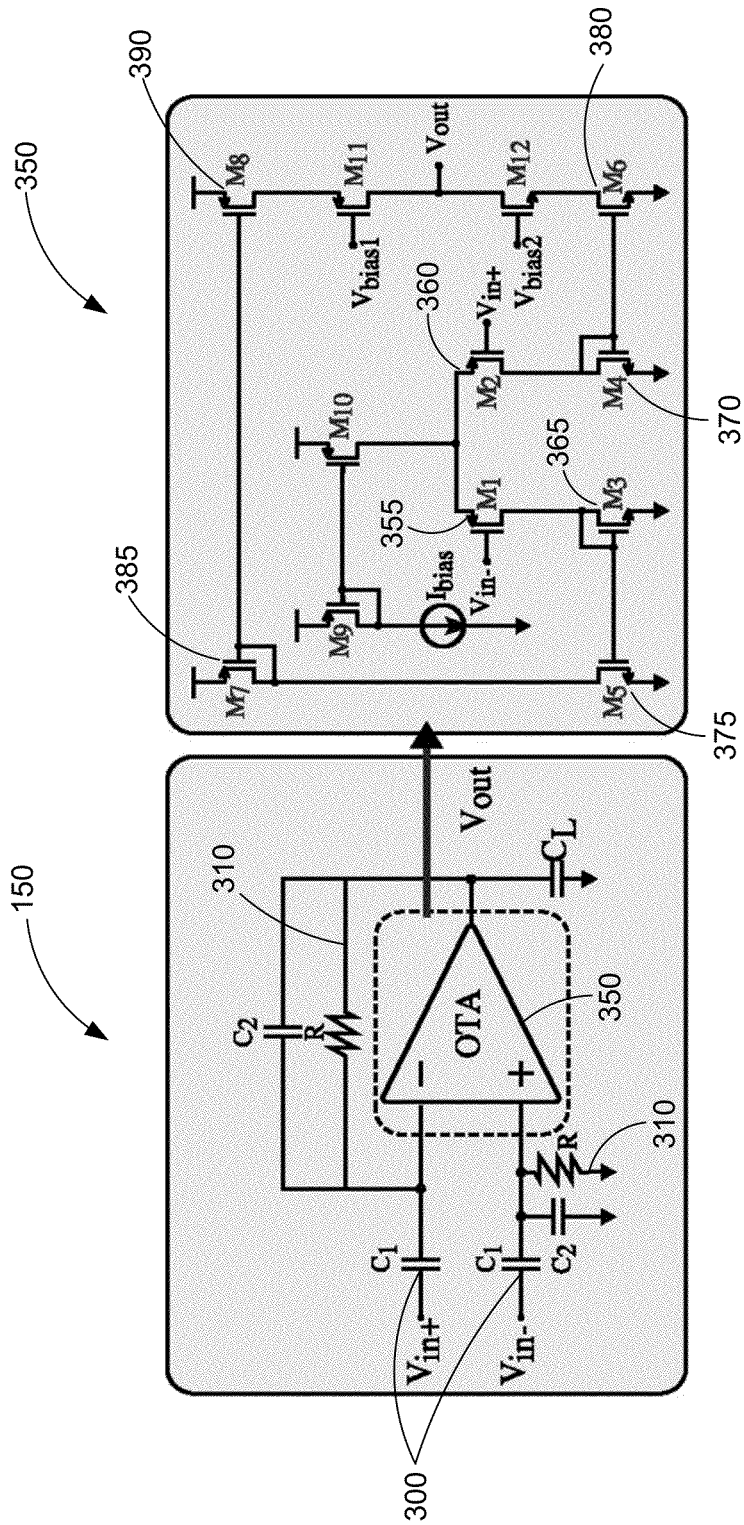

The sensitivity of the sensor 110 is determined primarily by the noise level of the front-end amplifier 150. In addition, in various embodiments, the sensor 110 is configured such that the overall power consumption is sufficiently low so as to generate minimal temperature increase (relative to ambient) of the chip surface in contact with the sample. FIG. 4a shows a schematic diagram of amplifier 150 according to various embodiments [2]. The input capacitors 300 are used to reject dc, while the MOS transistors 310 in amplifier 150 work as pseudo-resistors [2]. This resistance is nonlinear, depending on the voltage difference across the transistors. The core of the amplifier is the operational transconductance amplifier (OTA) 350.

FIG. 4b illustrates a detailed schematic view of the OTA according to various embodiments. In some embodiments, input PMOS devices 355 and 360 are utilized and are designed to have large gate areas are used in the OTA to reduce 1/f noise. Transistors 355 and 360 are designed to operate in the subthreshold region, while transistors 365, 370, operate in strong inversion to minimize the effect of the noise in transistors 365, 370 on the input-referred noise [2]. In various embodiments, the over-all gain of the amplifier 150 is 40 dB with a measured bandwidth of 0.35 to 70 Hz; and input-referred noise of $0.3 pV^2/Hz$ at 1 Hz.

Figure 5:
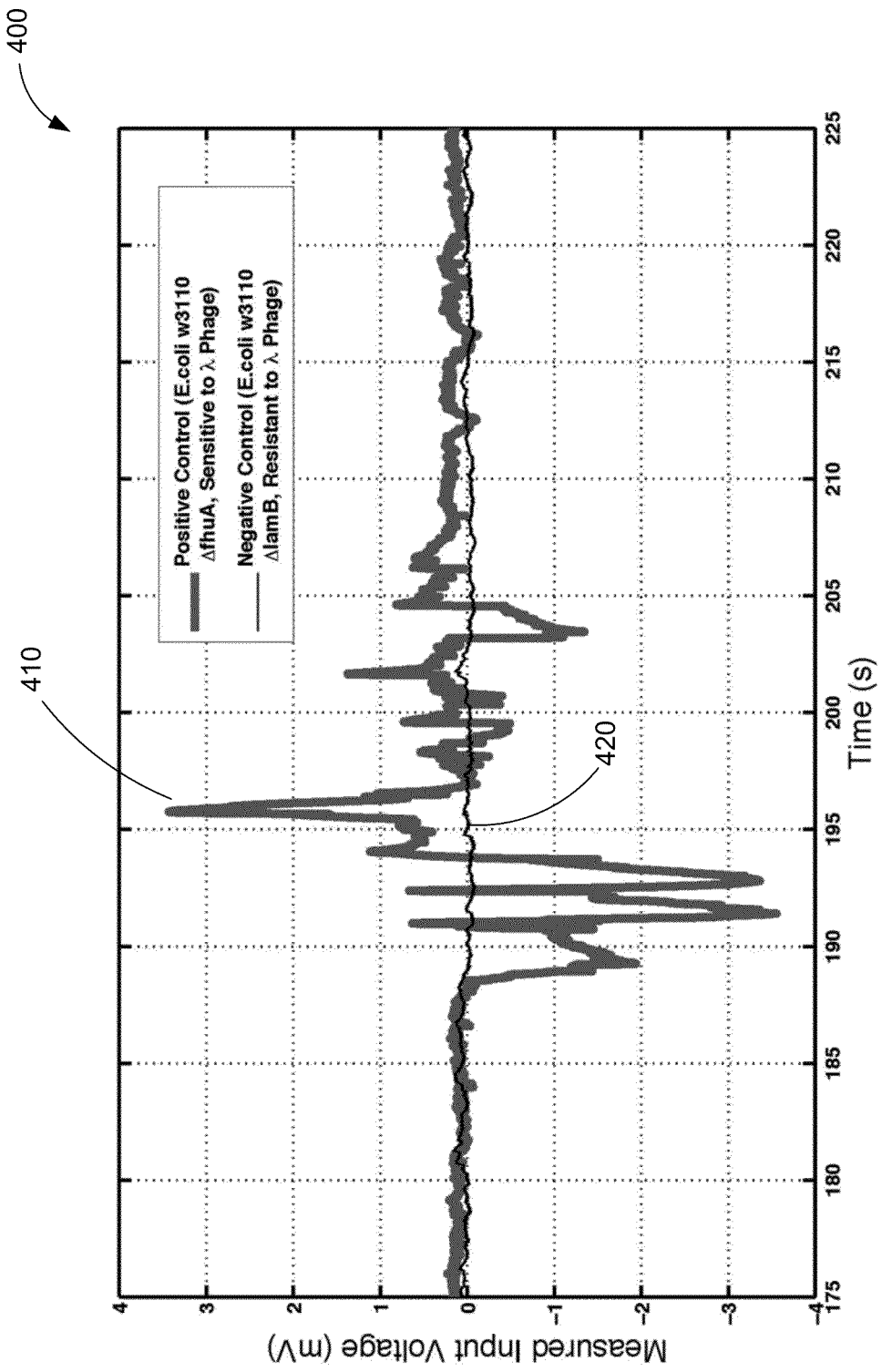
FIG. 5 is a graph of the time domain measured input voltage when sensitive and insensitive cells are mixed with λ phage in a 50 second time window.

In some embodiments, the chips can be encapsulated to isolate the bond wires from the sample, leaving only the electrodes exposed. The inventors utilized such embodiments in a series of experiments. The experiments were performed using $\lambda$ $cl_{857}Sam_7$ phage and two bacterial strains; E. coli w3110 $\Delta$fhuA is sensitive to the $\lambda$ phage (positive control) and E. coli w3110 $\Delta$lamB is resistant (negative control). Both positive and negative control bacteria have an optical density (OD) of approximately 0.7 (i.e., concentration ~$10^8$ cells/mL). The experiment starts by mixing 10 μL of bacteria with 5 μL of the $\lambda$ phage. The mixture is then applied to the chip surface and the output of the amplifier is digitized from one to seven minutes. The ambient temperature in the experiments was 23.1° C. FIG. 5 shows a time window 400 of the measured sensor output signal for both sensitive and resistant bacteria when mixed with $\lambda$ phage. Plot 410 corresponds to the measured input voltage for the sensitive bacteria. Plot 420 corresponds to the measured input voltage for the resistant bacteria. The large spikes on the sensitive graph correspond to the time when a bacterium is attacked by the phage. These spikes occur throughout the measurement interval, mainly in the first 5 minutes after mixing the sensitive cells with phage. The noise on the resistant cell sample is mainly due to amplifier noise and random noise introduced from the fluid via the electrodes. The significance of performing tests with both sensitive and resistant bacteria is to demonstrate the specificity of the system to a certain bacteria, without false positives. Additional electrodes on the die were directly connected to external (off-chip) instrumentation amplifiers and simultaneously measured the input fluctuations confirming the on-chip measurement results.

Figure 6:
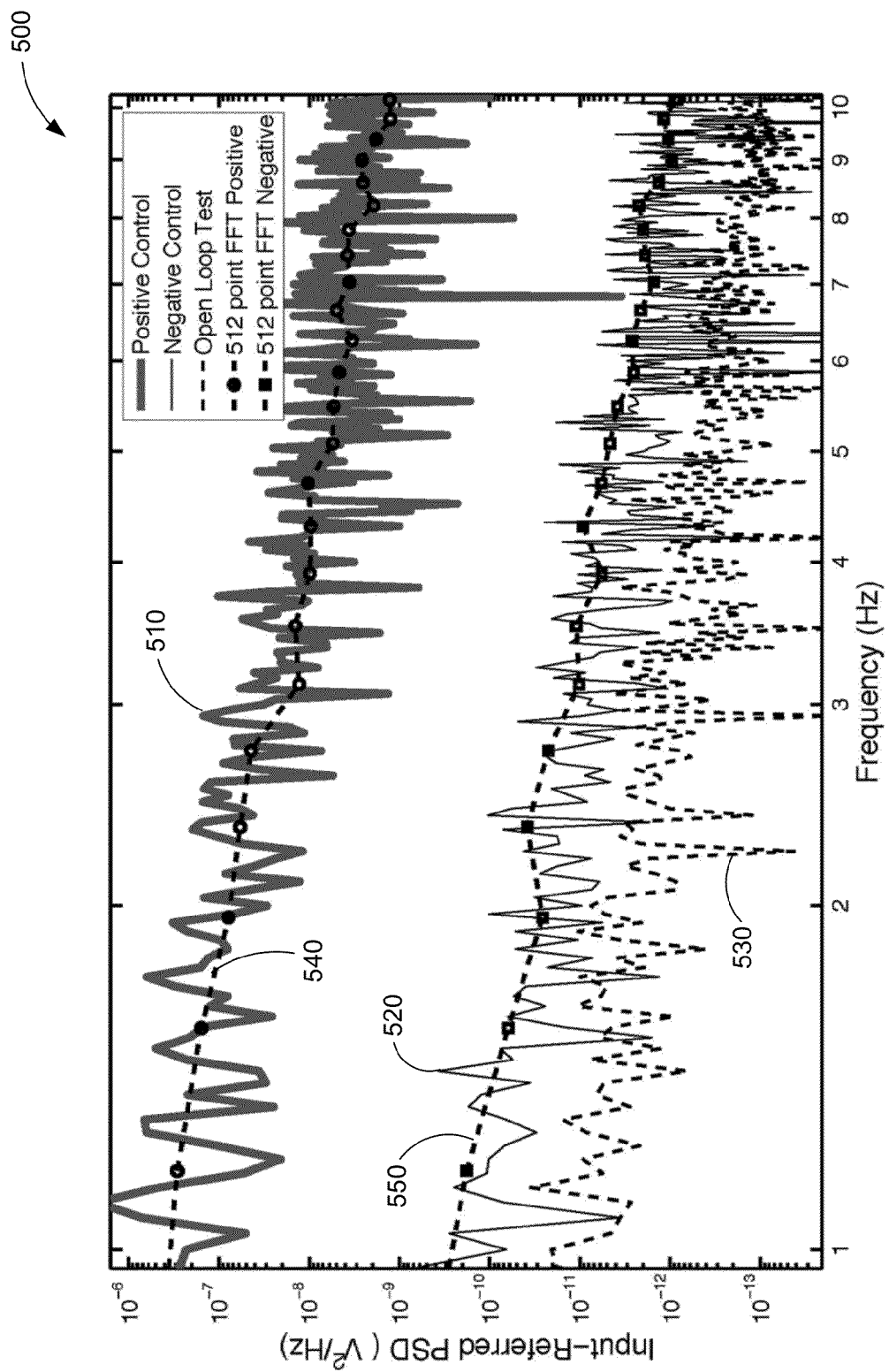
FIG. 6 is a graph of the power spectral density of the input-referred signal for positive and negative controls and the open loop test results.

An alternative method, for easier assessment of the time domain measurements, is to compute the power spectral density (PSD) of the observed signal [1]. FIG. 6 shows the PSD of the measured voltage fluctuations over 1 to 10 Hz for both sensitive (plot 510) and resistant bacteria (plot 520). FIG. 6 also illustrates the open-loop PSD plot 530, which corresponds to the experiment where no sample was applied to the chip. FIG. 6 also illustrates, for reference purposes, the PSD computed using 512-point Fast Fourier Transform (FFT) for the sensitive (plot 540) and resistant (plot 550) bacteria. This will be discussed in greater detail below. The noise level after applying the sample (negative control) to the electrodes is slightly higher than the open-loop test results, while the PSD of the positive control signal shows large frequency components in the 1 to 10 Hz band.

In various embodiments, the chip can be fabricated in 0.18 μm CMOS technology using thick-oxide transistors and consumes 122 μW with a 3.3V supply for two recording channels. FIG. 7a shows a micrograph of a chip 600 according to various embodiments. Chip 600 comprises a plurality of electrodes 140 and amplifiers 150. FIG. 7b is an enlarged view of a portion of FIG. 7a, showing the electrodes in greater detail. FIG. 7c illustrates a graph 650 that lists the specifications of chip 600. The two channels, each consisting of an electrode pair and an amplifier, are integrated on-chip along with controlling switches and circuits. Different size electrodes were also fabricated to explore the sensitivity of measured signals to electrode geometries. The experimental results achieved by the inventors show that a highly integrated sensor realized in standard CMOS can provide a low-cost (i.e., disposable), battery-operated handheld device for rapid detection of bacteria with excellent specificity and sensitivity.

In addition, in various embodiments, further steps may be taken to integrate the system further and make it more portable. For example, in some embodiments, a micro-fluidic package may be added to transport the bacteria sample to the electrodes. More specifically, in some embodiments, microfluidic channels could be used to guide fluid to the measurement site that contains the electrodes. The use of such channels can prevent the liquid from spilling out into areas other than the test site and from contaminating the environment outside of the chip. This may be particularly advantageous when the fluid sample may contain dangerous bacteria.

In addition, other embodiments could be implemented by integrating an on-chip ADC and a digital post-processing block to create the PSD signature for use by a classifier to identify the presence of a specific bacterial strain. In portable applications, computational speed may not be an issue and therefore in some embodiments a low-speed ultra-low-power FFT block can be used to compute the FFT, with less than 155 nJ/FFT as reported in [3]. A sampling frequency of 200 Hz with a frequency precision of 0.5 Hz would need a 512-point FFT for this application. As mentioned above, for reference, shown in FIG. 6 are plots 540 and plot 550, each of which is the PSD of the recorded signals obtained by averaging over 512-point FFT blocks that have been computed with 16-bit fixed-point precision.

Although FIG. 7a illustrates chip 600 as having a single measurement site (i.e. a single area on the chip having electrodes), other embodiments can have a greater number of measurement sites. As an example not intended to be limiting, a chip could be manufactured having five measurement sites. Table 650 of FIG. 7 indicates a table for an embodiment with a single measurement site and having 2 channels. Embodiments with a greater number of measurement sites could have a greater number of channels.

Although the description above focused on the use of a particular phage and bacterium, it is not intended to exclude the use of other phages or bacteria. Moreover, it is not intended to exclude other appropriate antibacterial agents that may kill, destroy or incapacitate bacteria by for example attacking their cell walls. Appropriate antibacterial agents may include, but are not limited to, phage ghosts, phage tail-like bacteriocins (PTLBs), antimicrobial peptides, bacteriophage lytic enzymes, and bactericidal antibiotics.

Specifically, Phage ghosts are bacteriophage particles that are lacking nucleic acid. These particles have the ability to depolarize the cell membrane and cause leakage of ions out of the cell. One can potentially generate phage ghosts from any phage particle by knocking the DNA out of the head by for example but not limited to treating with EDTA.

With respect to Phage Tail-Like Bacteriocins (PTLBs), approximately 96% of previously described phages have a tail that mediates host cell interaction and serves as a conduit for nucleic acid injection during infection. A variety of phage tails have been shown to be lethal to their bacterial hosts, even in the absence of other phage components. Most strikingly, *Pseudomonas* bacterial species naturally produce specialized phage tail-like molecules, called R- or F-pyocins, that are lethal to other *Pseudomonas* strains and related species. Other species that produce tail-like bacteriocins include, but are not limited to, *Erwinia, Serratia, Budvicia, Pragia, Bacillus, Rhizobium, Xenorhabdus, Yersinia*, and *Streptomyces*. Genetically engineered PTLBs may be derived from any phage tail-like particle or naturally occurring bacteriophage tail.

Antimicrobial peptides are short proteins that are naturally produced or chemically synthesized and exhibit a range of activities, including solubilization of the bacterial cell membrane. They are useful against Gram positive and negative microorganisms.

Bacteriophage lytic enzymes are protein molecules naturally produced by phage to destroy the bacterial cell wall to allow the release of phage progeny. These enzymes are specific for the species or strain from which they were produced.

In addition it should be noted that chip 600, as well as other embodiments of sensor 110 may be used with a variety of antibacterial agents. More specifically, many embodiments need not be altered to be compatible with different types of bacteria or antibacterial agents.

In various embodiments each chip 600 may be prepared prior to testing a sample of bacteria by applying an appropriate antibacterial agent to the testing site (electrodes). For example, but not limited to, the antibacterial agents mentioned above may be applied to the electrodes.

As explained above, various embodiments of sensor 110 or sensor system 100 can be used to identify particular types of bacteria by for example utilizing specific phages. Various embodiments of sensor 110 or sensor system 100 can also be used test the effectiveness of particular type of antibacterial agents in destroying bacteria, which may operate by for example destroying the cell walls of the bacteria. For example, a sample may be known to contain bacteria, which can be applied to the measurement sites of the sensor 110, and an antibacterial agent of unknown effectiveness can be applied to the measurement site in order to test its effectiveness.

Embodiments of sensor 110 can be used at clinics or hospitals in order to quickly determine the effectiveness of a particular antibacterial agent in killing a bacterium causing an infection in a patient. Alternatively, embodiments of sensor 110 can be used at clinics or hospitals in order to quickly identify the type of bacterium or bacteria causing infections in a patient. In either case, the healthcare professional(s) can as a result quickly (on site) identify a specific and targeted treatment for the infection, in a much faster time frame as compared to sending a sample to a laboratory for analysis. Once this determination has been made, a very specific antibiotic could be selected instead of a broad-spectrum antibiotic, which may cause other bacteria to be killed. For example, in the case of an infection in a patient's gastrointestinal tract, it may be desirable to treat the patient with a very specific and targeted antibiotic as opposed to a broad-spectrum antibiotic in order to avoid killing bacteria that are beneficial to the health of the patient.

Figure 8A:
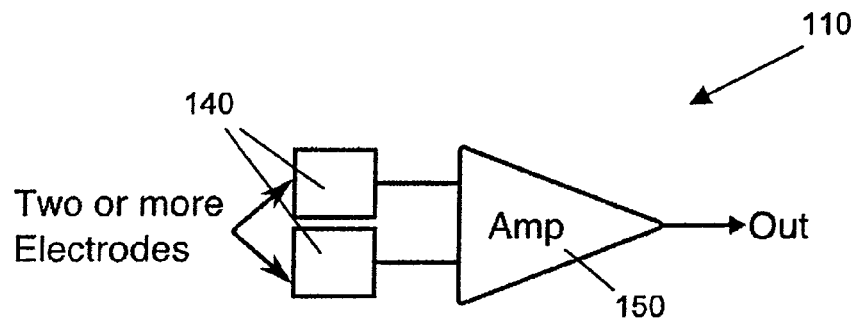
FIG. 8a is a block diagram of the sensor of FIG. 2, according to various embodiments of applicants' teachings.

Reference is now made to FIGS. 8a to 8g, each of which illustrate a sensor according to various embodiments of applicants' teachings. FIG. 8a illustrates sensor 110 of FIG. 2 without the data acquisition system. However, as will be explained below additional elements can be included in the sensor. More specifically these other elements can be integrated on the same substrate as the sensor as will be discussed in greater detail below. In the various embodiments illustrated in FIGS. 8a to 8g, the single substrate realization of all components can allow for the mass fabrication of a complete working sensor or sensor system at very high volumes and low cost and with high selectivity and sensitivity.

Figure 8B:
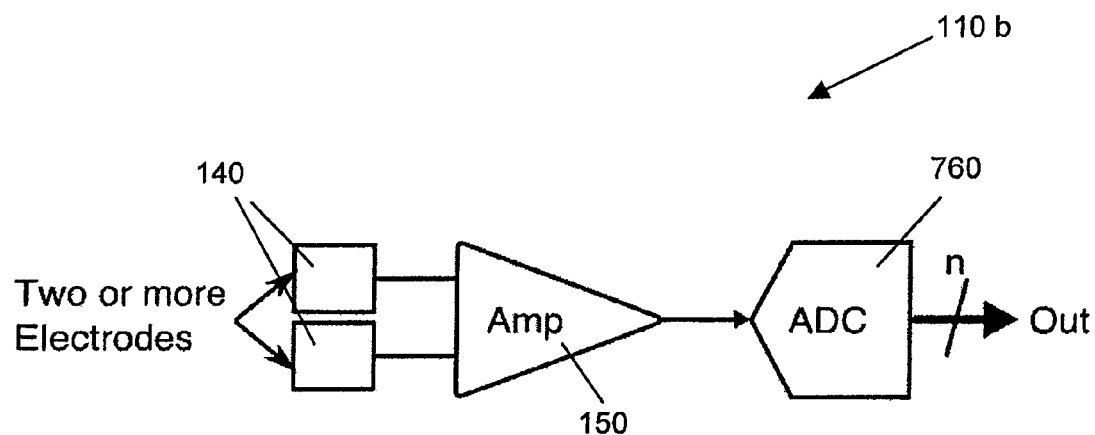
FIG. 8b to 8g are block diagrams of a sensor according to various other embodiments of applicant's teachings.

FIG. 8b illustrates various embodiments of sensor 110b. Sensor 110b comprises electrodes 140, amplifier 150 and also includes an analog to digital converter (ADC) 760, each of which can be integrated on a single substrate. In such embodiments, the corresponding data acquisition system (not illustrated), in contrast to data acquisition system 120 for sensor 110, would not include an ADC.

Figure 8C:
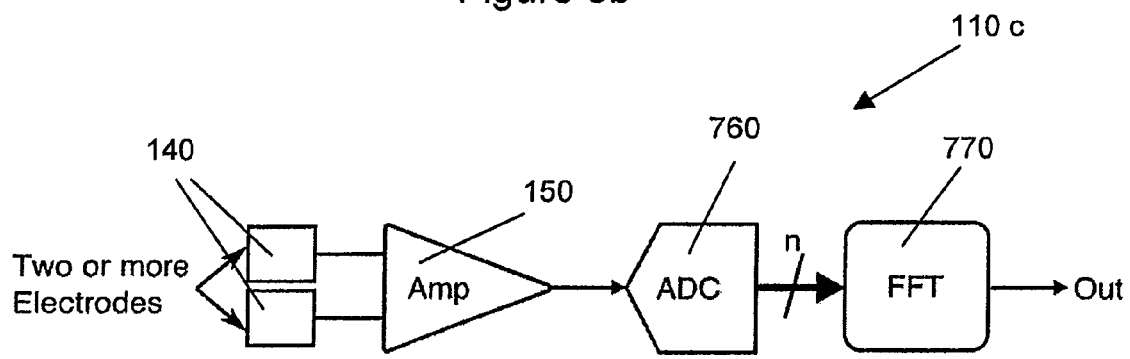

FIG. 8c illustrates various embodiments of sensor 110c. Sensor 110c comprises electrodes 140, amplifier 150, ADC 760, and a Fast Fourier Transform circuit 770, each of which can be integrated on a single substrate. In such embodiments, the corresponding data acquisition system (not illustrated), in contrast to data acquisition system 120 for sensor 110, would not include an ADC. It will be understood that Fast Fourier Transform circuit 770 is a digital circuit.

Figure 8D:
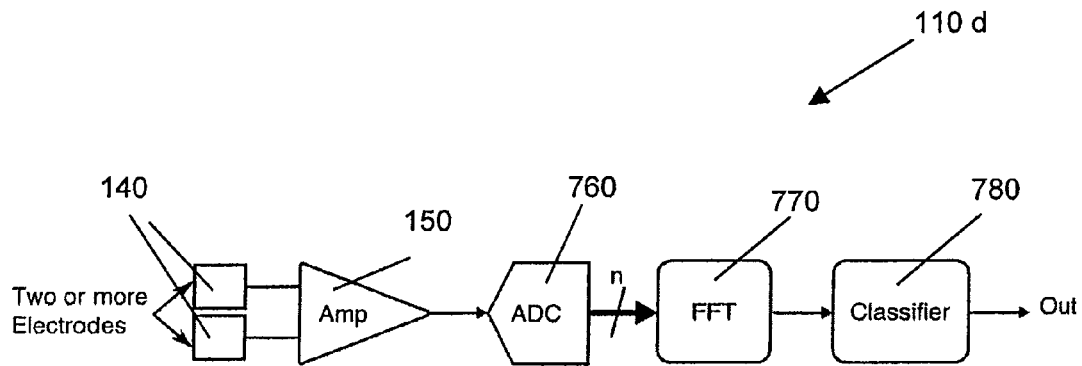

FIG. 8d illustrates various embodiments of sensor 110d. Sensor 110d comprises electrodes 140, amplifier 150, ADC 760, a Fast Fourier Transform circuit 770, and a classifier 780, each of which can be integrated on a single substrate. In such embodiments, the corresponding data acquisition system (not illustrated), in contrast to data acquisition system 120 for sensor 110, would not include an ADC. It will be understood that Fast Fourier Transform circuit 770 and classifier 780 are digital circuits.

Figure 8E:
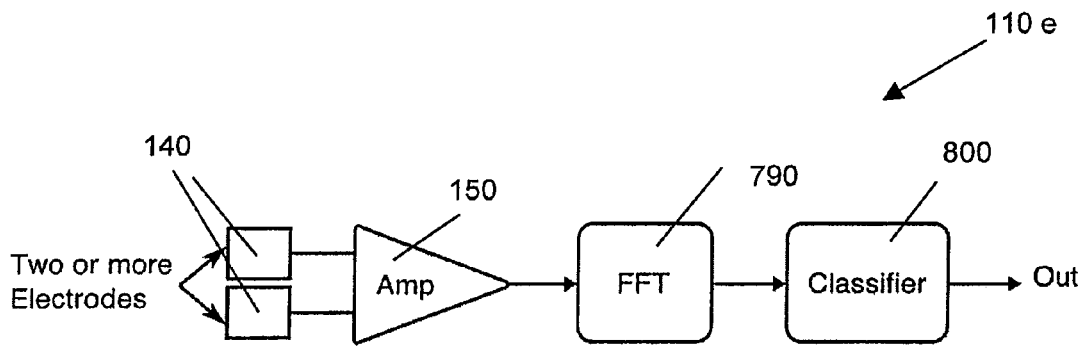

FIG. 8e illustrates various embodiments of sensor 110e. Sensor 110e comprises electrodes 140, amplifier 150, a Fast Fourier Transform circuit 790, and a classifier 800, each of which can be integrated on a single substrate. It will be understood that Fast Fourier Transform circuit 790 and classifier 800 are analog circuits.

Figure 8F:
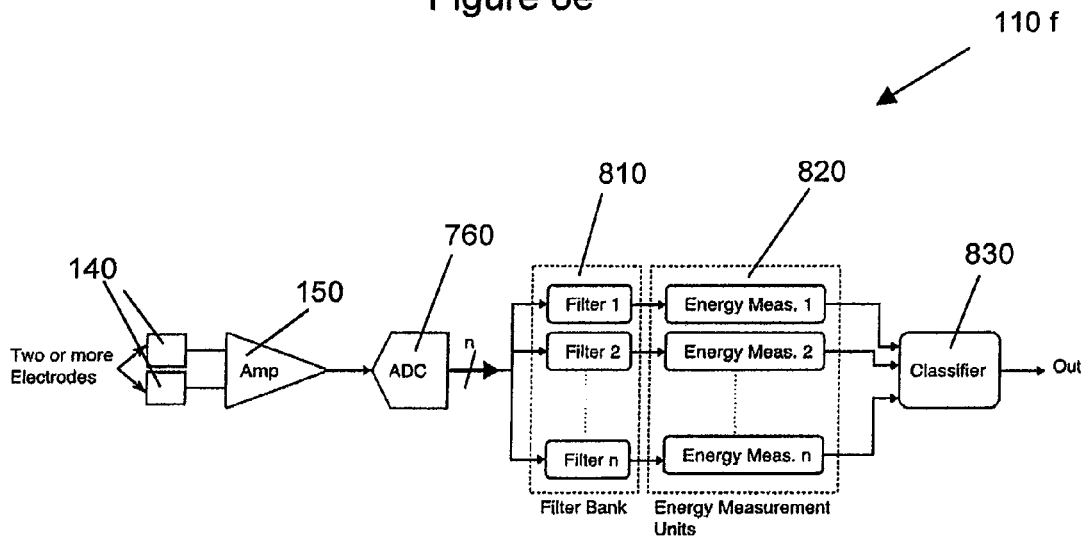

FIG. 8f illustrates various embodiments of sensor 110f. Sensor 110f comprises electrodes 140, amplifier 150, ADC 760, a filter bank 810, a plurality of energy measurement units 820, and a classifier 830, each of which can be integrated on a single substrate. In such embodiments, the corresponding data acquisition system (not illustrated), in contrast to data acquisition system 120 for sensor 110, would not include an ADC. It will be understood that filter bank 810, energy measurement units 820, and classifier 830 are digital circuits.

Figure 8G:
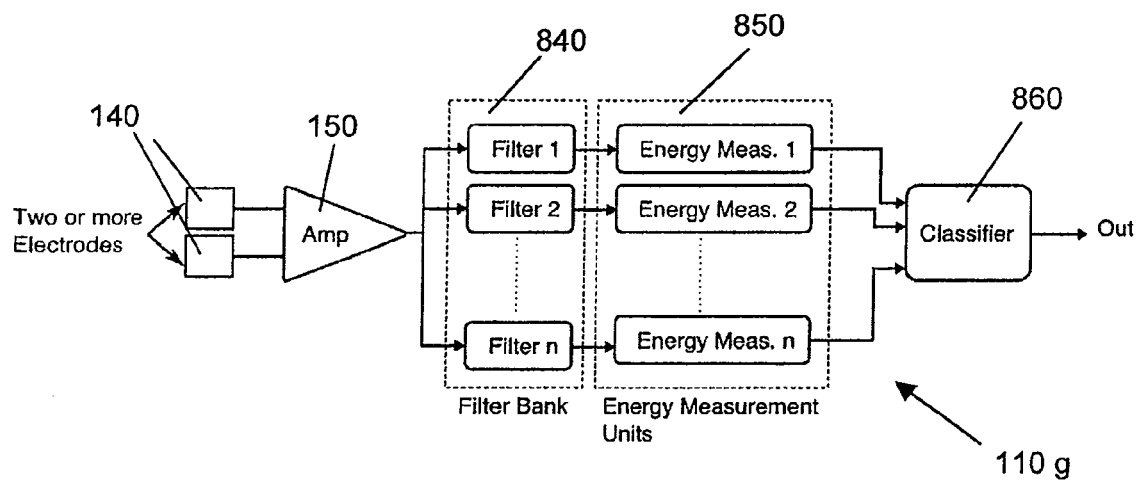

FIG. 8g illustrates various embodiments of sensor 110f. Sensor 110g comprises electrodes 140, amplifier 150, a filter bank 840, a plurality of energy measurement units 850, and a classifier 860, each of which can be integrated on a single substrate. It will be understood that filter bank 840, energy measurement units 850, and classifier 860 are analog circuits.

It should be understood that in some embodiments, the digital circuits referred to in FIGS. 8b to 8c can be hardwired in nature. In various other embodiments, the digital circuits referred to in FIGS. 8b to 8c can be implemented using a program controlled architecture that is programmable in nature. In some other embodiments, the digital circuits referred to in FIGS. 8b to 8c can be implemented using both a hardwired and a program controlled architecture.

It should be understood that in some embodiments, the analog circuits referred to in FIGS. 8b to 8c can be continuous time analog circuits. In various other embodiments, the analog circuits referred to in FIGS. 8b to 8c can be discrete time analog circuits.

It should be understood that in alternate embodiments (not shown), an integrated sensor may be provided which includes only one electrode. That is, a sensor may be provided that is similar to sensor 110, however only one electrode may be provided, and measurements may be made with respect to ground or with respect to a fixed potential. In such embodiments, a well may or may not be included in the sensor.

EXAMPLE

1. Introduction

This work presents a new method for detecting bacteria using pyocins as biological detecting elements along with electrical noise detection using integrated circuits implemented in a generic 0.18 μm CMOS process. This work successfully demonstrates detection of two strains of *P. aeruginosa*. It also presents measurement results for different concentrations of *P. aeruginosa* in the sample. In addition, a new, more efficient, signal processing technique for bacterial identification and for estimating the concentration is presented.

Figures 9A, 9B, 9C:
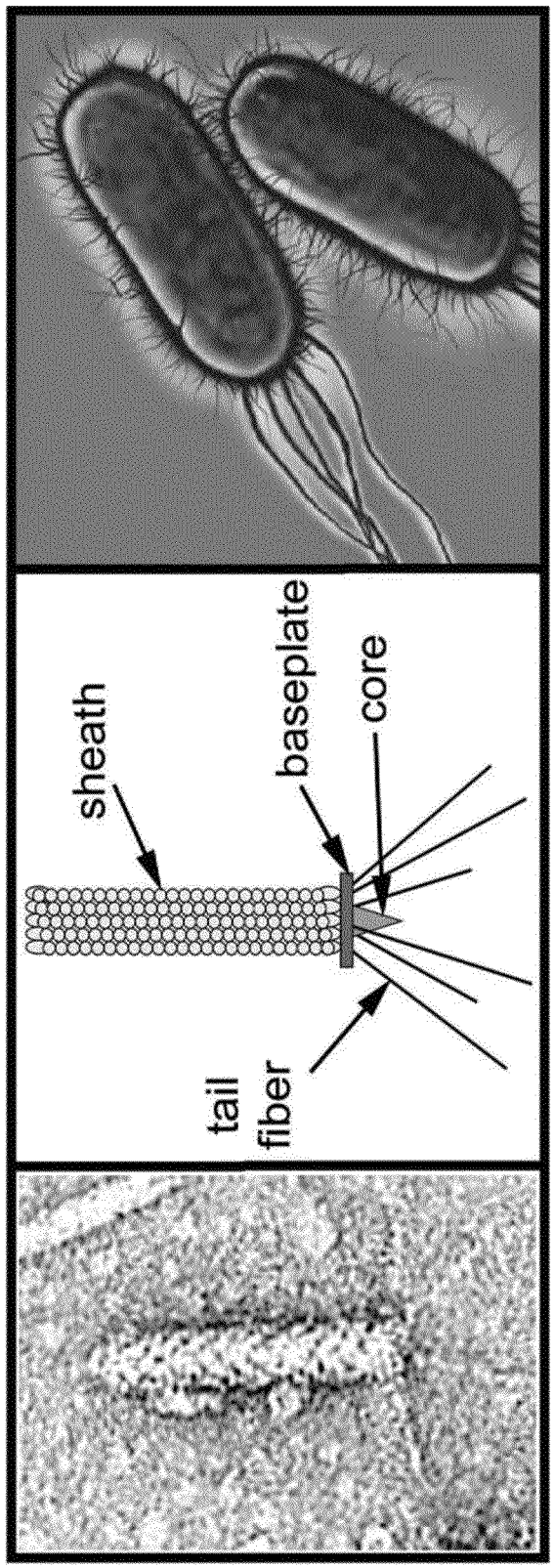
FIG. 9A is an electron micrograph of R-type pyocin in accordance with Example 1 described hereinbelow.
FIG. 9B is a diagram of pyocin structure in accordance with Example 1 described hereinbelow.
FIG. 9C shows *Pseudomonas aeruginosa* in accordance with Example 1 described hereinbelow

Pyocins are bacteriocins produced by *Pseudomonas* strains (they're produced by many non-aeruginoas *Pseudomonas* species) that are lethal to other strains of the same or related species. R-type pyocins are bacteriophage tail-like bacteriocins as shown in FIGS. 9A-9C ([8] and [9]). When an R-type pyocin attacks its host bacterial cell, it binds to the outer surface of the cell, and undergoes sheath contraction and core penetration through the cell membrane. This results in the efflux of ions from inside the cell and ultimately in death of the cell. Unlike bacteriophages, pyocins have no DNA and are not able to replicate. The host range of the pyocin is determined by the specific binding of the tail fibers to the receptors on the surface of the bacteria. The tail fibers can be engineered to control the host range of the pyocin and be used to detect any bacterial strain of interest. An advantage of R-type pyocin over bacteriophage is that, unlike bacteriophage, it does not repair the hole produced by its penetration into the cell membrane. This results in the rapid, irreversible escape of ions from inside of the cell.

This ion efflux results in electric field fluctuations in the sample that can be detected to identify the presence of a cell sensitive to the pyocin.

2. System Block Diagram and Circuits

Figures 10A, 10B:
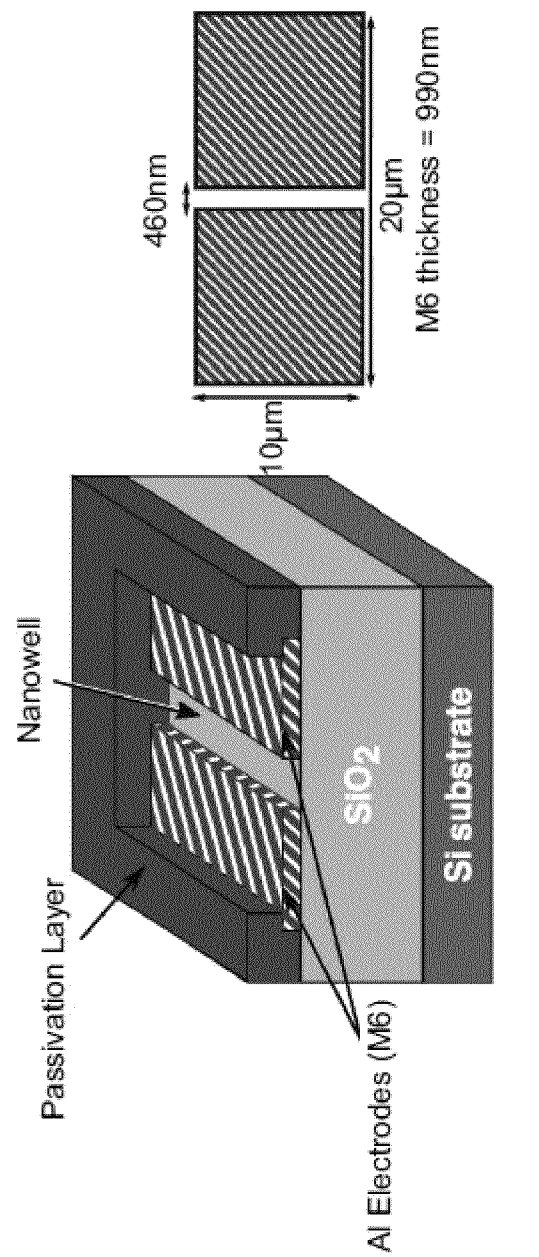

The voltage fluctuations in the sample are picked up by the integrated nanowell implemented in the CMOS chip. The nanowell is constructed using two top-metal electrodes (metal 6 in the process used) with a defined gap between them. The trench is formed by removing the passivation layer on top of the electrodes and the gap using the passivation mask similar to the technique for exposing top metal for pads. FIGS. 10A and 10B show the cross section of the CMOS chip with nanowell on top of it as well as the dimensions of the on-chip electrodes used in the measurements. The height of the nanowell is defined by the thickness of the top metal layer of the process. A noble top metal is not applied on top of the Al electrodes in the CMOS process and hence post-fabrication processing is not required.

Figure 11A:
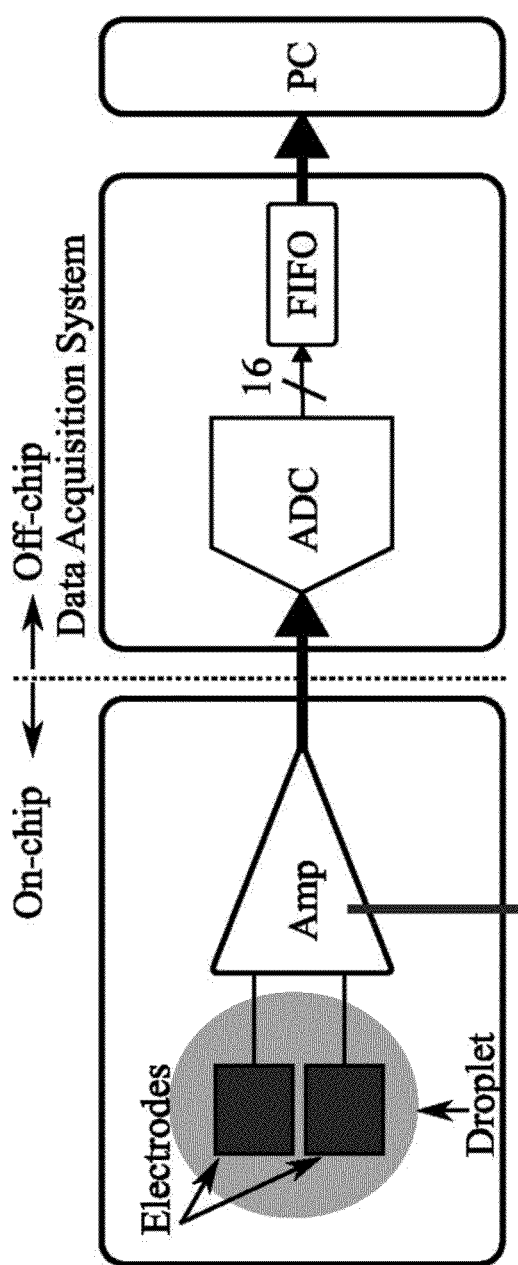
FIG. 11a is a system block diagram of an sensor in accordance with Example 1 described hereinbelow.
Figure 11B:
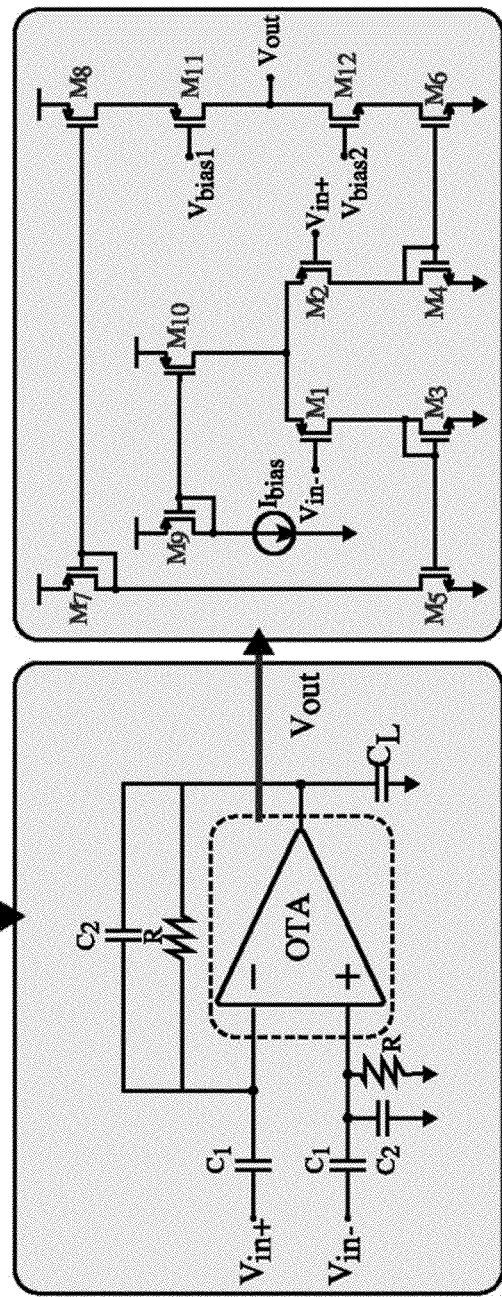
FIG. 11b is a schematic diagram of an amplifier and OTA in accordance with Example 1 described hereinbelow.

FIGS. 11A and 11B show the system block diagram of the sensor. The electrodes are connected to on-chip amplifiers for signal enhancement. The measured gain of the amplifiers is 40 dB within the bandwidth of 0.35 to 70 Hz and their input-referred noise is 0.3pV2/HZ at 1 Hz. The input capacitors provide the dc decoupling between the input of the amplifier and the electrodes and the resistors in parallel with C2 define the lower bandwidth of the amplifier. The resistors are implemented using MOS transistors as described in [2] to provide very large resistors in parallel with C2 with low area overhead. The aluminum oxide on the electrodes also results in a series capacitor with C1 and its effect is negligible. The amplifier is designed for low power and low noise operation and is similar to the one used in [6].

The output of the on-chip amplifiers are connected to a PC for signal analysis through a data acquisition system. The off-chip data acquisition system digitized the amplified signal and sends the data through a FIFO to the PC.

Figure 12:
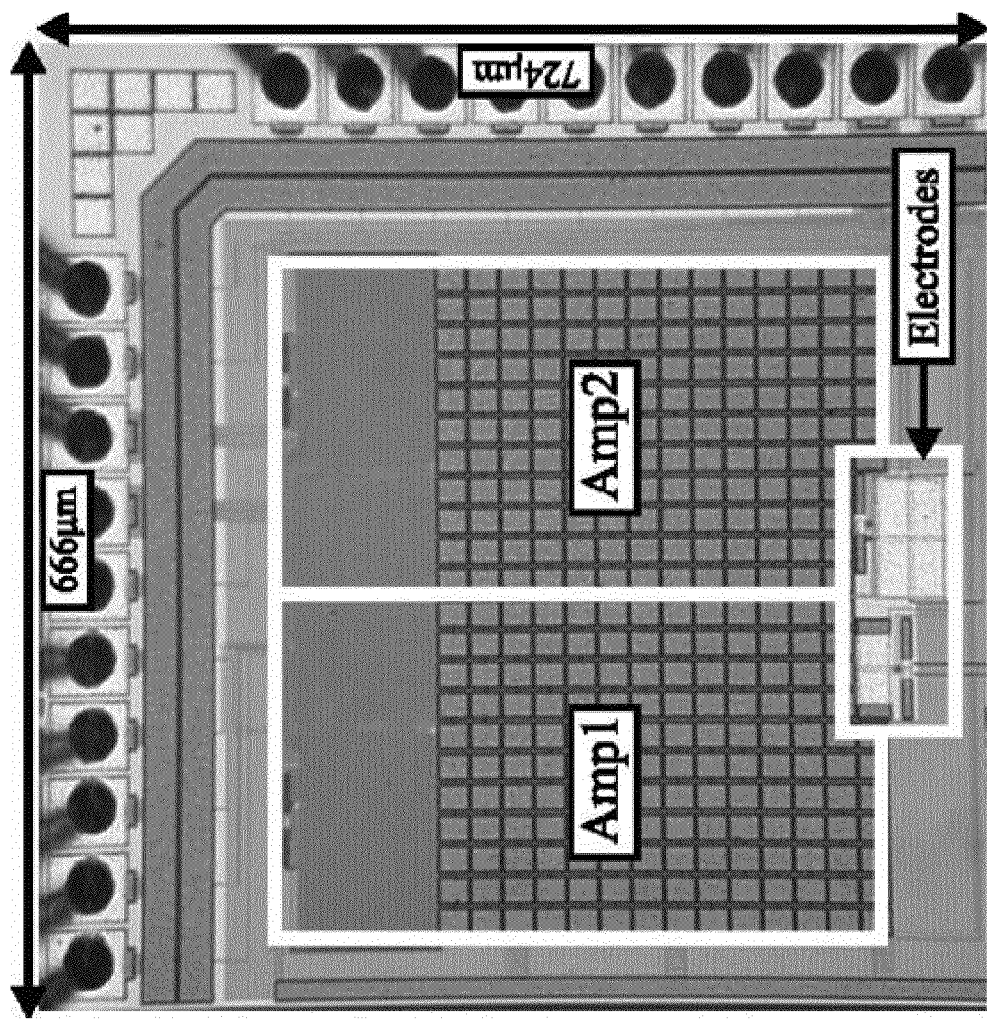
FIG. 12 is a micrograph of an fabricated chip in accordance with Example 1 described hereinbelow.

The chip was fabricated in a standard TSMC 0.18 μm CMOS process with 6 metal and 1 poly layers. Two channels with their corresponding electrodes and amplifiers were fabricated on the chip with total power consumption of 122 μW @ 3.3V power supply and total die area of 0.482 mm2. FIG. 12 shows the micrograph of the chip. Other electrodes are also included in the chip and also some of the electrodes are connected to off-chip amplifiers to confirm the correct functionality of the on-chip amplifiers.

3. Measurement Setup and Experimental Protocol

The chips were encapsulated to isolate the bonding wires from contact with the liquid sample leaving the electrodes exposed.

Figures 13A, 13B:
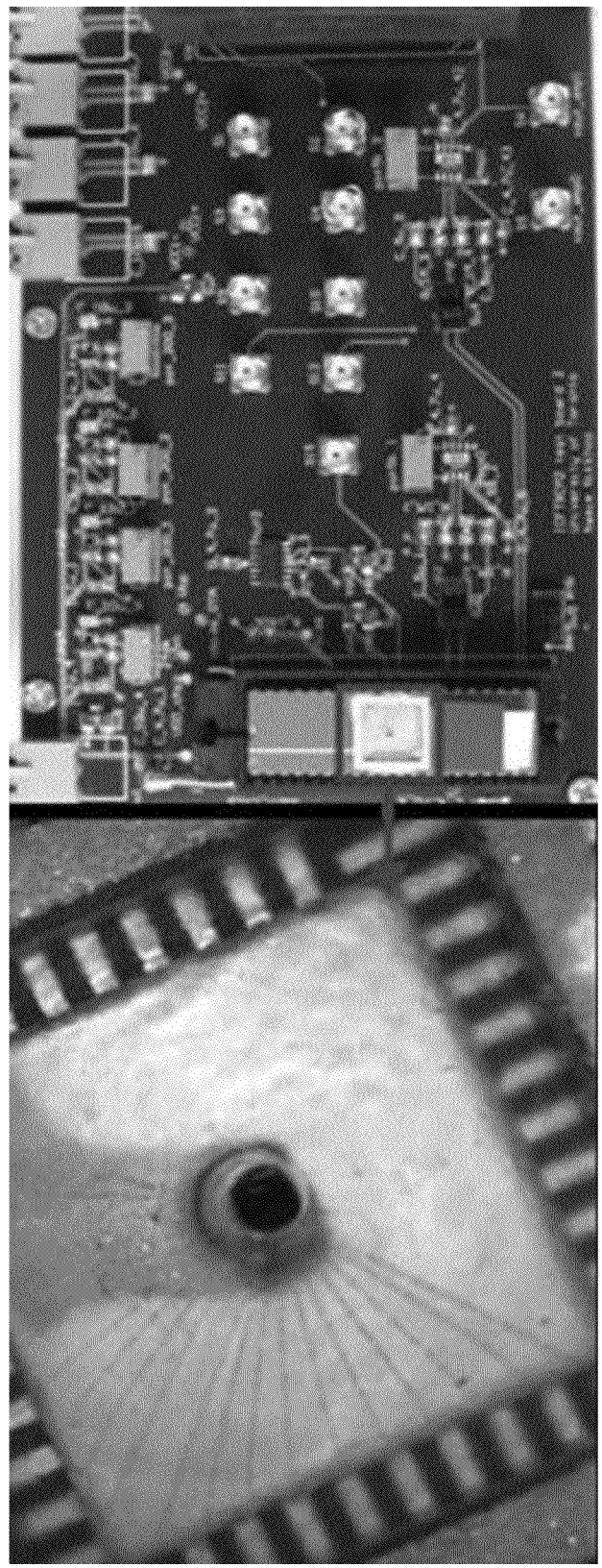
FIG. 13a is a photograph of an integrated circuit with encapsulated bonding wires in accordance with Example 1 described hereinbelow.
FIG. 13b is a photograph of an test-board in accordance with Example 1 described hereinbelow.

A mixture of Jet Acrylic liquid and Jet Denture Repair acrylic, purchased from [7], was used for encapsulation. This epoxy mixture, used in dental repair, is biologically inert. FIGS. 13A and 13B show the test setup with the encapsulated chip and the supporting printed circuit board.

Each experiment was performed by mixing 5 µL of the pyocin with 10 µL of the target bacteria. After mixing the pyocin and sample, 10 µL of the mixture was applied to the chip surface. The output voltage of the amplifier was recorded starting from 1 minute after the mixture occurred and total recording time was 6 minutes.

The pyocins used in these experiments were isolated from the *Pseudomonas* strain PA01, which is known to produce both F- and R-type pyocins. Two different strains of *P. aerugionsa* were used in the measurements, PAC64 and PAC10. These strains were grown overnight, then subcultured and grown to mid-log phase. The PAC64 and PAC10 cells are sensitive to the pyocin; PA01 is a separate strain from PAC64 and PAC10. Each chip was used only once in order to avoid any signal modifications due to previous contamination.

4. Experimental Results

A. PAC 10 cells and PA01 Pyocin

Figure 14:
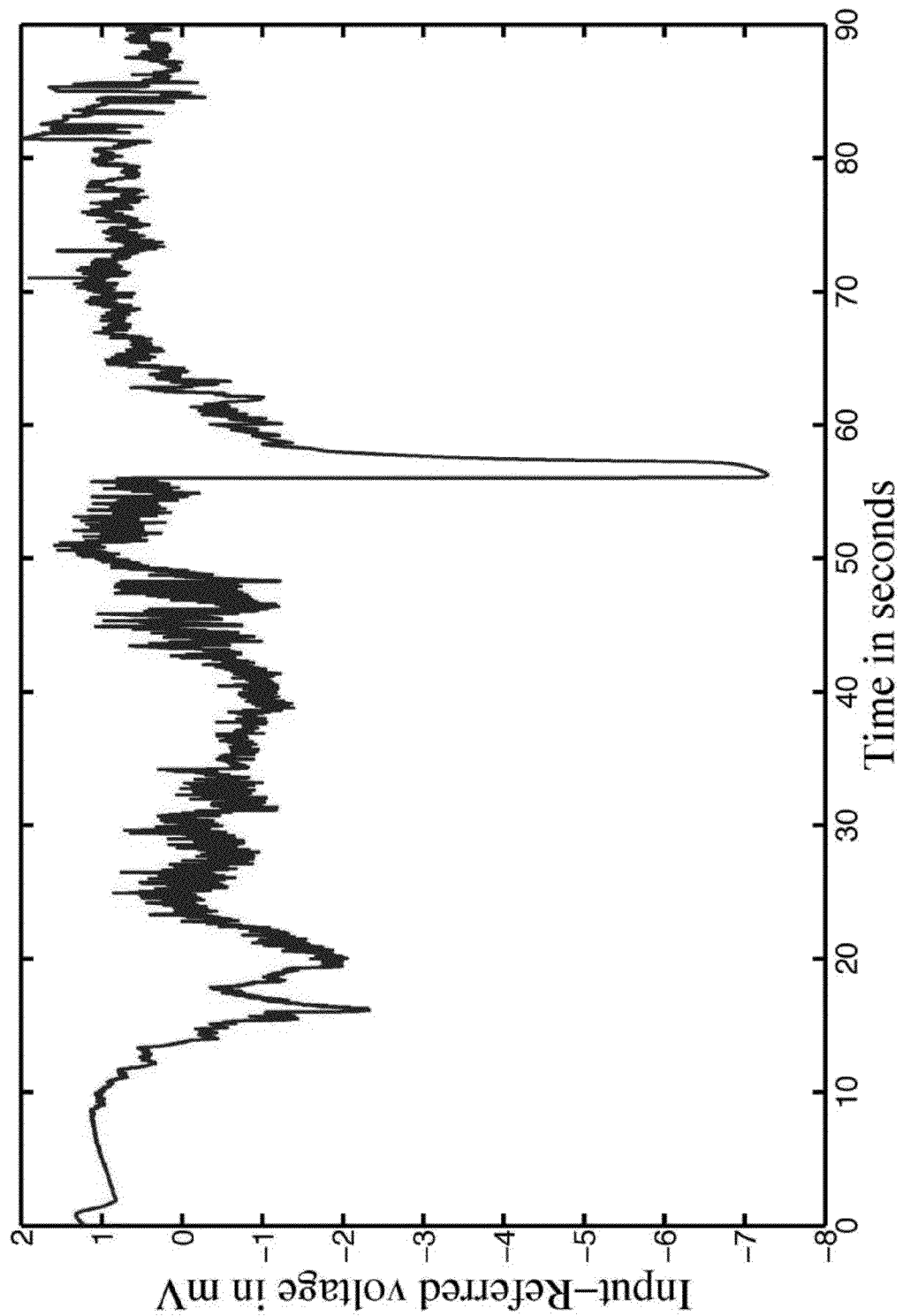
FIG. 14 is a graph of a 90-second window of the time-domain input voltage fluctuations when PAC10 cells with OD=0.7 are mixed with PA01 cells (time origin is from the start of recording time) in accordance with Example 1 described hereinbelow.

The first set of experiments were performed by mixing PAC10 cells with PA01 pyocin. The PAC10 cells in this experiment have OD of approximately 0.7 which corresponds to a cell concentration of approximately 108 CFU/ml. FIG. 14 shows a 90-second window of the total 6 minute recording interval of the measured input voltage over time. When the sensitive *Pseudomonas* strain is mixed with the pyocin, the input voltage fluctuations occur during the time interval of the killing event. Unlike the infection mechanism of bacteriophages against bacteria as used in [6], the ion leakage from inside the bacteria due to pyocin attachment likely continues until the cells die. This results in continuous, ling-lived spikes at the output even beyond 10 minutes. The number of the spikes and the amplitude of the fluctuations are also dependent on the concentration of the *Pseudomonas* cells in the sample. FIG. 14 shows that the presence of the specific *Pseudomonas* strain can be detected by observing the time-domain input voltage when sensitive *Pseudomonas* cells are mixed with specific pyocin.

Figure 15:
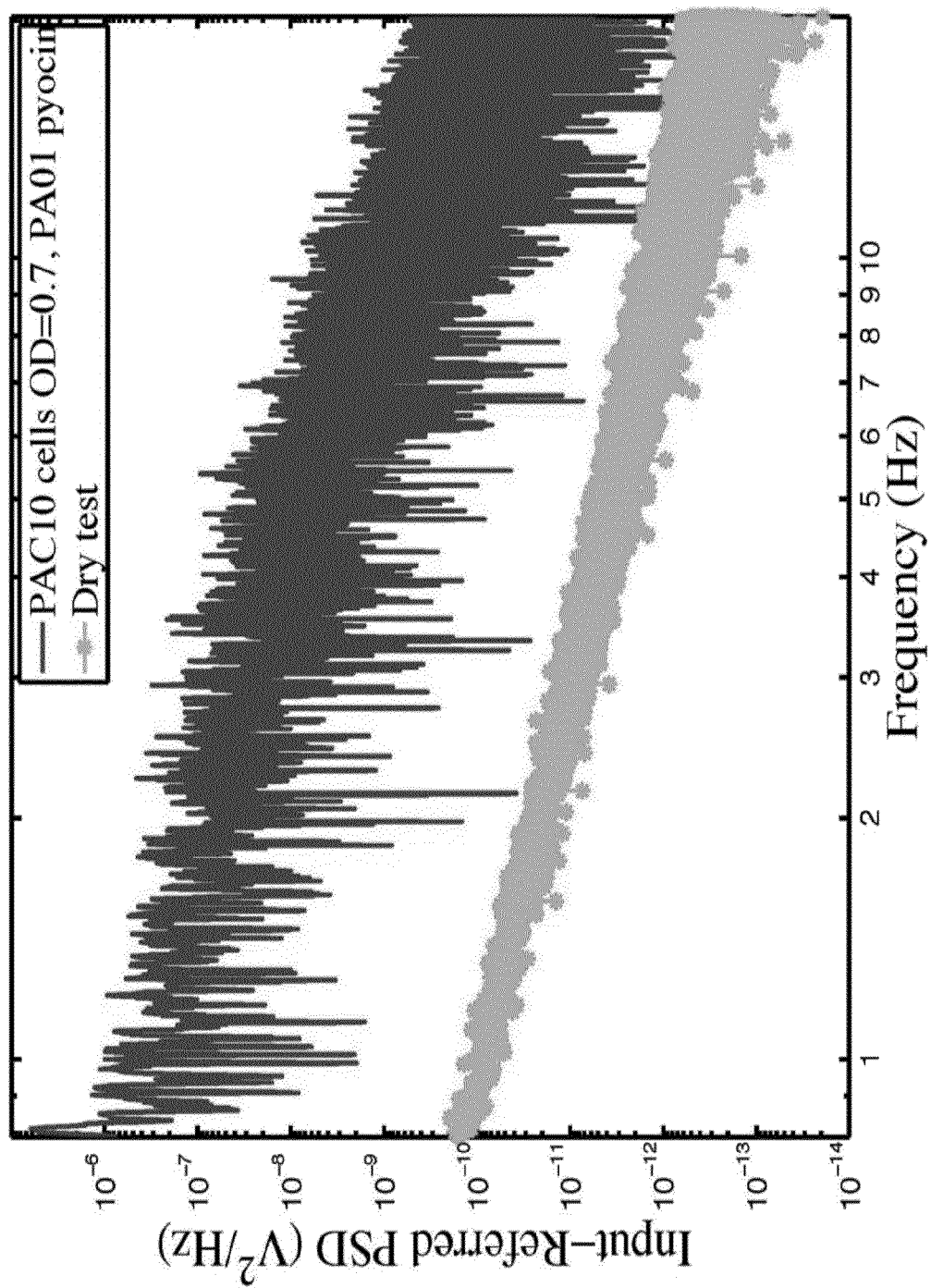
FIG. 15 is an graph of power spectral density of the input voltage in dry test and when mixture PAC10 OD=0.7 and PA01 are applied in accordance with Example 1 described hereinbelow.

Computing the power spectral density (PSD) of the input voltage is a technique used in [1] and [6] to identify the presence or absence of the target bacterial strain. The PSD of the input voltage was computed for two experiments in FIG. 15. The bottom line shows the input PSD when no analyte is applied to the chip surface (dry test). The top lines in FIG. 15 show the input PSD, when the mixture of PA01 pyocins and sensitive PAC10 cells were applied to the chip surface, in the frequency range of 1 to 10 Hz. It is clear that increased PSD level in this band can be used as an indication of the presence of the pyocin targeted host cell.

PAC64 cells and PA01 Pyocin

Figure 16:
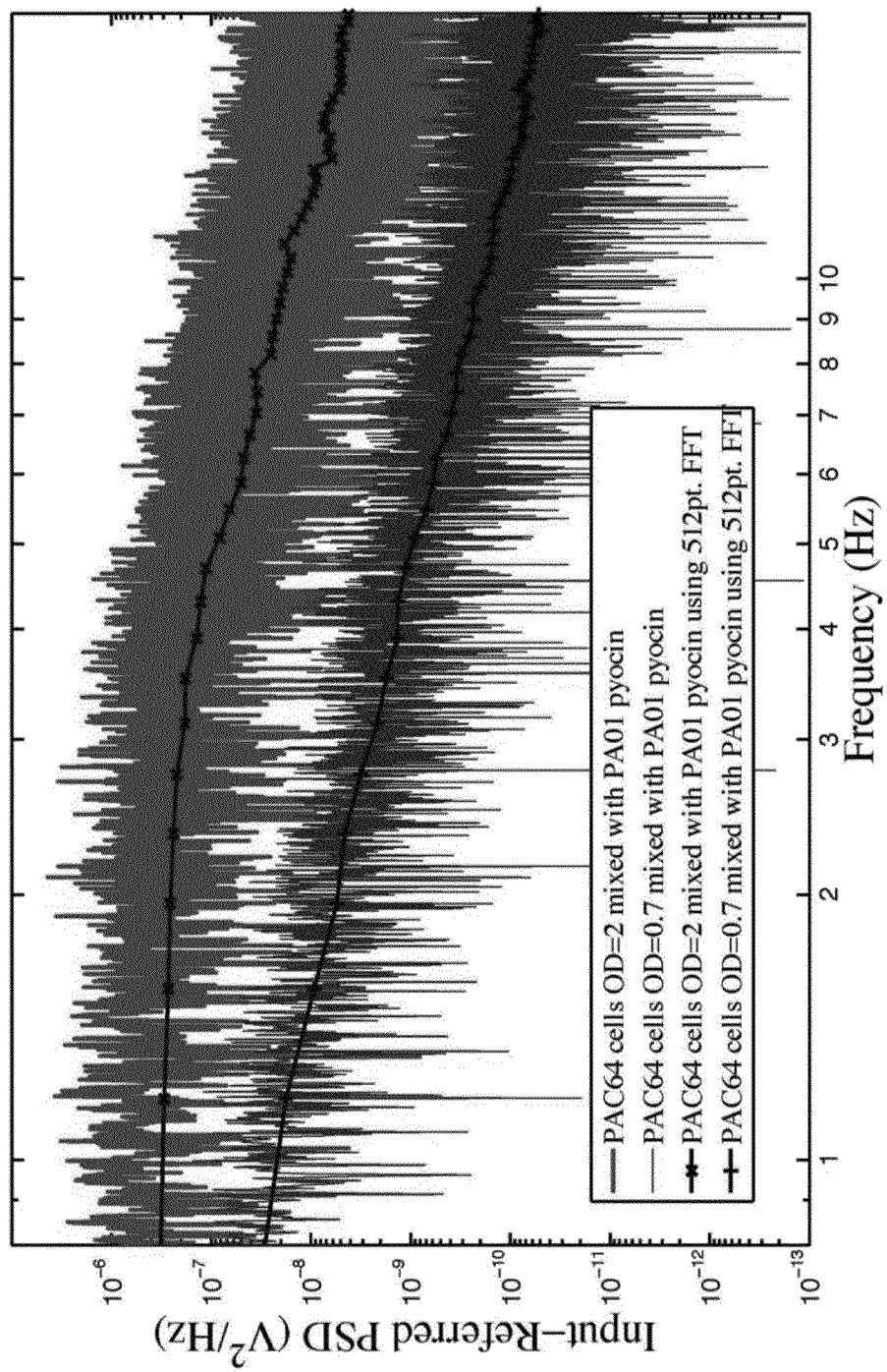
FIG. 16 is an graph of PSD for a large number of sample points and also for a 512-point FFT for the mixture of two different concentrations of PAC64 with PA01 pyocin in accordance with Example 1 described hereinbelow.

A second set of experiments was performed by mixing another strain of *P. aeruginosa*, PAC64, with the PA01 pyocins. Two different concentrations of PAC 64 were used in two experiments to show the dependency of the input-referred PSD in a 1 to 10 Hz band to the concentration of the cells. In the first experiment, the PAC64 cells with OD=2 were mixed with PA01 pyocins and data was collected for 6 minutes. The input voltage fluctuations in this experiment were larger with an increased number of spikes and a longer duration of noise activity. FIG. 16 shows the PSD of the input voltage fluctuations for this measurement.

In another experiment, the PAC64 cells with OD=0.7, which corresponds to concentration of approximately 108 CFU/ml, were mixed with pyocins and data was collected as mentioned before. FIG. 16 also shows the input PSD for this experiment. From FIG. 16 it can be observed that there is an increased level of noise when mixing either of PAC64 and PAC10 *Pseudomonas* cells with PA01. Thus, the presence of both sensitive strains can be confirmed by observing the input-referred PSD alone. FIG. 16 also shows that the energy of the fluctuations in a 1 to 10 Hz frequency band are much stronger in the higher concentration experiment (OD=2) than the lower concentration (OD=0.7). This is due to an increased number of spikes in the 6-minute recording interval as well as a higher amplitude of the fluctuations.

The solid lines in FIG. 16 show the input-referred power spectral density, computed using a 512-point FFT with 50% overlap. The sampling frequency of the data samples is 200 Hz and hence a 512-point FFT is sufficient for 0.5 Hz FFT resolution. The solid lines in FIG. 16 show that conventional 512pt. FFT signal processing operations are sufficient to reveal the PSD threshold level required to identify the presence or absence of bacteria and also to get an estimate of the concentration of the bacterial cells in the sample without any additional signal processing circuit complexity. Previously reported [3], ultra-low-power CMOS realizations of a 512-point FFT can be co-integrated with the sensor reported here because of the low sampling frequency requirements (200 Hz), further enabling the low power consumption specifications of a portable device.

Figure 17:
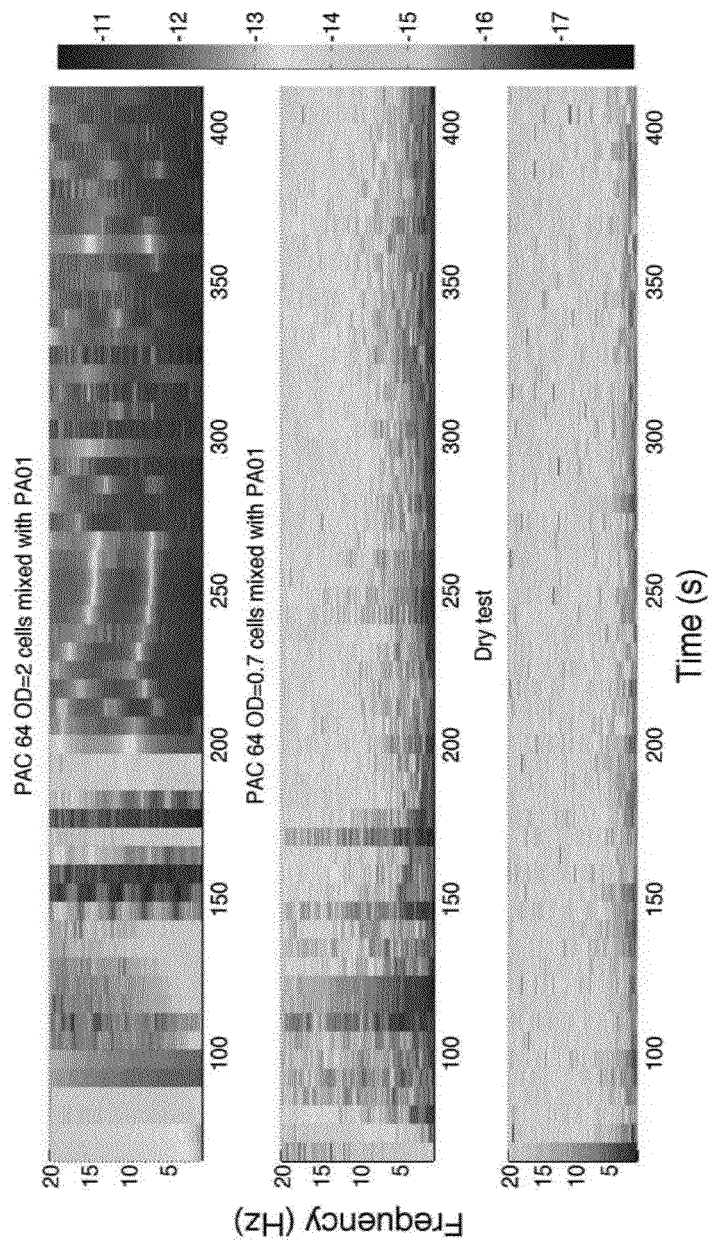
FIG. 17 is a spectogram of the input voltage over recording time and frequency.

The input voltage spikes are picked up by the nanowell when a bacteria is close to the electrodes; the sequence of fluctuations are random in amplitude and in time of occurrence. Looking at the spectrogram of the input voltage over time with an appropriate FFT time window provides a more accurate representation of the level and distribution of the fluctuations and ultimately the relative concentration of the cells. FIG. 17 shows the spectrogram of the input over time from 1 to 20 Hz where the input PSD is calculated over a window of 10 seconds with 4 seconds of overlap. The PSD levels are presented by a color that is proportional to log 10 (PSD). In this figure, the location of fluctuations are easily distinguished by the red color (high PSD level) versus quiet locations that have blue bars corresponding to low PSD. This method can conveniently be used to identify the presence of the cells as well as estimate the concentration of the cells.

5. Conclusion

A 0.18 µm CMOS integrated circuit provides an integrated lab-on-chip solution for the rapid identification of bacteria. It combines the specificity of pyocins as the biological detecting elements and sensitivity afforded by low-power CMOS circuits and was used to experimentally identify *P. aeruginosa* bacteria in less than 10 minutes. The effect of bacterial cell concentration is also presented in the experimental results. The CMOS chip does not require any post processing or gold metal deposition, enabling low-cost mass-production, while the low-power nature of the design allows battery-powered, portable realizations.

While the applicants' teachings are described in conjunction with various embodiments, it is not intended that the applicants' teachings be limited to such embodiments. On the contrary, the applicants' teachings encompass various alternatives, modifications, and equivalents, as will be appreciated by those of skill in the art.

An additional example relating to the Applicant's teachings can be found in "A 0.18 μm CMOS Integrated Sensor for the Rapid Identification of Bacteria", published at the 2008 IEEE International Solid-State Circuits Conference, ISSCC 2008/Session 18/MOS Medley/18.4, which is incorporated herein by reference in it's entirety.

REFERENCES

[1] M. D. King, S. Seo, J. U. Kim, et al., "Rapid Detection and Identification of Bacteria: Sensing of Phage-Triggered Ion Cascade (SEPTIC)", J. of Biological Physics and Chemistry, 5, no. 1, pp. 3-7, January 2005.
[2] R. Harrison, "A Low-Power Low-Noise CMOS Amplifier for Neural Recording Applications", J. Solid-State Cir., vol. 28, no. 6, pp. 958-965, June 2003.
[3] A. Wang, and A. Chandrakasan, "A 180 mV Subthreshold FFT Processor Using a Minimum Energy Design Methodology", J. Solid-State Cir., vol. 40, no. 1, pp. 310-319, January 2005.
[4] Y.-T. Chang, Dept. of Chemistry, New York University, "T4 Phage". Accessed on Nov. 6, 2007, <http://www.nyu.edu/classes/ytchang/book/e002.html>.
[5] Phage Research Group, Evergreen State College, "Phage Attachment to *E. Coli* Cell Wall". Accessed on Nov. 6, 2007, <http://academic.evergreen.edu/projects/phage/>.
[6] N. Nikkhoo, C. Mann, K. Maxwell and P. G. Gulak, "A 0.18 μm CMOS Integrated Sensor for the Rapid Identification of Bacteria", ISSCC Digest of Technical Papers, pp. 336-337, February 2008
[7] Central Dental Ltd., <http://www.centraldentalltd.com/>
[8] S. R. Williams, D. Gebhart, D. W. Martin, and D. Scholl, "Retargeting R-Type Pyocins to Generate Novel Bactericidal Protein Complexes", J. of Applied and Environmental Microbiology, vol. 74, no. 12, pp. 3868-3876, June 2008
[9] Roche Diagnostics, copyright F. Hoffman-La Roche Ltd., "*Pseudomonas Aeruginosa*", January 2008, Accessed on Jul. 14, 2008, http://www.roche.com/home/media/med_background-info/med_backgr-sepsis.htm

We claim:

1. A sensor for detecting an electric field fluctuation associated with the permeabilization of a bacterial cell wall, the sensor comprising:
    a substrate with a top-layer passivation layer;
    at least two electrodes integrated on the substrate exposed by an opening in the passivation layer, the substrate and the at least two electrodes defining a well between the at least two electrodes, and the at least two electrodes being configured to generate a signal in response to an electric field fluctuation in close proximity to the well triggered when at least one antibacterial agent associated with the well contacts a cognate target;
    an amplifier integrated on the substrate and configured to generate an amplified signal in response to the signal;
    a plurality of electrical connectors comprising polysilicon and/or metal wiring layers separated by appropriate insulating layers with appropriate vias and contacts for electrically connecting the at least two electrodes and the amplifier;
    wherein the substrate, the at least two electrodes, the amplifier and the electrical connectors form a CMOS circuit; and
    a processor electrically connected to the amplifier to analyze the amplified signal.

2. The sensor of claim 1 wherein the processor is integrated on the substrate.

3. The sensor of claim 2 wherein the substrate, the at least two electrodes, the amplifier and the processor form a CMOS circuit.

4. The sensor of claim 1 wherein the processor performs an orthogonal transformation of the amplified signal.

5. The sensor of claim 4 wherein the orthogonal transformation is a Fast Fourier Transform (FFT).

6. The sensor of claim 4 wherein the processor computes the power spectral density and/or the spectrogram of the amplified signal to measure the concentration of the cognate target.

7. The sensor of claim 1 wherein the processor comprises at least one filter.

8. The sensor of claim 1, wherein the processor further comprises:
    an energy measurement unit configured to measure the energy of the amplified signal; and
    at least one threshold detector configured to detect when the measured energy signal reaches a predetermined threshold.

9. The sensor of claim 1, wherein the processor further comprises:
    an energy measurement unit configured to measure the energy of the amplified signal; and
    a classifier.

10. The sensor of claim 1, wherein the processor further comprises analog components.

11. The sensor of claim 1 further comprising an analog to digital converter electrically connected to the amplifier, the analog to digital converter configured to digitize the amplified signal.

12. The sensor of claim 11 wherein the analog to digital converter is integrated on the substrate.

13. The sensor of claim 1 wherein the well is characterized by a distance between the at least two electrodes, the distance being between approximately 500 nanometers and approximately 50 micrometers.

14. The sensor of claim 1 wherein the well is characterized by a distance between the at least two electrodes, the distance being between approximately 20 nanometers and approximately 500 nanometers.

15. The sensor of claim 1 wherein the processor is integrated on a second substrate.

16. The sensor of claim 1 further comprising an analog to digital converter electrically connected to the amplifier and the processor, the analog to digital converter integrated on a second substrate and configured to digitize the amplified signal.

17. The sensor of claim 1 wherein the substrate is selected from the group consisting of silicon, single-crystal silicon, amorphous silicon plastic, polymer, glass, sapphire, quartz, silica, silicon carbide, zinc oxide, magnesium oxide, manganese oxide, germanium, gallium nitride, gallium arsenide, gallium phosphide, indium phosphide, polysilicon, n-type diffusion semiconductor material, and p-type diffusion semiconductor material.

18. The sensor of claim 1 further comprising at least one noble metal which is applied to the at least two electrodes.

19. The sensor of claim 1 further comprising a power supply to power the sensor.

20. The sensor of claim 19 wherein the power supply receives energy wirelessly from a remote location.

21. The sensor of claim 20 further comprising at least one coupling capacitor configured to receive the energy through capacitive coupling.

22. The sensor of claim 21 wherein the at least one coupling capacitor is integrated on the substrate.

23. The sensor of claim 21 further comprising a rectifier and a storage capacitor configured to rectify and store the received energy.

24. The sensor of claim 23 wherein the storage capacitor is integrated on the substrate.

25. The sensor of claim 20 further comprising at least one coupling inductor configured to receive the energy through inductive coupling.

26. The sensor of claim 25 wherein the at least one coupling inductor is integrated on the substrate.

27. The sensor of claim 19 further comprising a wireless transmitter electrically connected to the processor, the wireless transmitter configured to transmit at least one of the amplified signal and the analyzed signal to a remote site.

28. A kit for detecting an electric field fluctuation associated with the permeabilization of a bacterial cell wall, the kit comprising:
the sensor of claim 1; and
at least one bacteriophage, positionable in close proximity to the well for triggering the electric field fluctuation when the at least one bacteriophage contacts a cognate target.

29. A kit for detecting an electric field fluctuation associated with the permeabilization of a bacterial cell wall, the kit comprising:
the sensor of claim 1; and
at least one phage ghost, positionable in close proximity to the well for triggering the electric field fluctuation when the at least one phage ghost contacts a cognate target.

30. A kit for detecting an electric field fluctuation associated with the permeabilization of a bacterial cell wall, the kit comprising:
the sensor of claim 1; and
at least one phage tail-like bacteriocin (PTLB), positionable in close proximity to the well for triggering the electric field fluctuation when the at least one bacteriophage contacts a cognate target.

31. A kit for detecting an electric field fluctuation associated with the permeabilization of a bacterial cell wall, the kit comprising:
the sensor of claim 1; and
at least one antimicrobial peptide, positionable in close proximity to the well for triggering the electric field fluctuation when the at least one antimicrobial peptide contacts a cognate target.

32. A kit for detecting an electric field fluctuation associated with the permeabilization of a bacterial cell wall, the kit comprising:
the sensor of claim 1; and
at least one bacteriophage lytic enzyme, positionable in close proximity to the well for triggering the electric field fluctuation when the at least one bacteriophage lytic enzyme contacts a cognate target.

33. A kit for detecting an electric field fluctuation associated with the permeabilization of a bacterial cell wall, the kit comprising:
the sensor of claim 1; and
at least one antibiotic, positionable in close proximity to the well for triggering the electric field fluctuation when the at least one antibiotic contacts a cognate target.

34. A method of utilizing the sensor of claim 1 to characterize a hypothesized antibacterial agent, the method comprising:
positioning at least one known bacteria in close proximity to the well or electrodes;
positioning the at least one hypothesized antibacterial agent in close proximity to the well or electrodes;
monitoring electric field fluctuations in close proximity to the well; and
characterizing the antibacterial agent based on the electric field fluctuations.

35. A method of utilizing the sensor of claim 1 to identify bacteria, the method comprising:
positioning at least one known antibacterial agent in close proximity to the well or electrodes;
positioning the at least one bacterium in close proximity to the well or electrodes;
monitoring electric field fluctuations in close proximity to the well or electrodes; and
identifying the at least one bacterium based on the electric field fluctuations.

36. A method of utilizing the sensor of claim 1 to characterize a hypothesized antibacterial agent, the method comprising:
positioning at least one known bacteria in close proximity to the well or electrodes;
positioning the at least one hypothesized antibacterial agent in close proximity to the well or electrodes;
monitoring electric field fluctuations in close proximity to the well; and
determining the efficacy of the antibacterial agent based on the electric field fluctuations.

* * * * *